(12) United States Patent
Cohen et al.

(10) Patent No.: US 10,036,016 B2
(45) Date of Patent: Jul. 31, 2018

(54) METHODS FOR INDUCING GLUCOSE UPTAKE

(71) Applicant: President and Fellows of Harvard College, Cambridge, MA (US)

(72) Inventors: Shenhav Cohen, Raanana (IL); Alfred L. Goldberg, Boston, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 15/021,495

(22) PCT Filed: Sep. 11, 2014

(86) PCT No.: PCT/IL2014/050810
§ 371 (c)(1),
(2) Date: Mar. 11, 2016

(87) PCT Pub. No.: WO2015/037001
PCT Pub. Date: Mar. 19, 2015

(65) Prior Publication Data
US 2016/0230171 A1    Aug. 11, 2016

Related U.S. Application Data

(60) Provisional application No. 61/876,929, filed on Sep. 12, 2013.

(51) Int. Cl.
*A61K 31/7115*  (2006.01)
*A61K 38/17*  (2006.01)
*C12N 15/113*  (2010.01)
*C07K 16/18*  (2006.01)

(52) U.S. Cl.
CPC ........ *C12N 15/113* (2013.01); *A61K 31/7115* (2013.01); *A61K 38/1709* (2013.01); *C07K 16/18* (2013.01); *C12N 2310/15* (2013.01); *C12N 2310/531* (2013.01)

(58) Field of Classification Search
None
See application file for complete search history.

(56) References Cited

U.S. PATENT DOCUMENTS 5,627,159 A * 5/1997 Shih ............... A61K 9/1272
424/450

OTHER PUBLICATIONS

Cohen et al., J Cell Biol. Aug. 20, 2012;198(4):575-589.*
Kariko et al., Nucleic Acids Res. Nov. 2011;39(21):e142.*

* cited by examiner

*Primary Examiner* — Daniel C Gamett
(74) *Attorney, Agent, or Firm* — Browdy and Neimark, PLLC

(57) ABSTRACT

The present invention provides a method for inducing glucose uptake in a muscle cell by inhibiting Trim32 protein in the cell and to a method for inducing glucose uptake in a muscle cell, by increasing the abundance of plakoglobin protein in the cell.

18 Claims, 10 Drawing Sheets

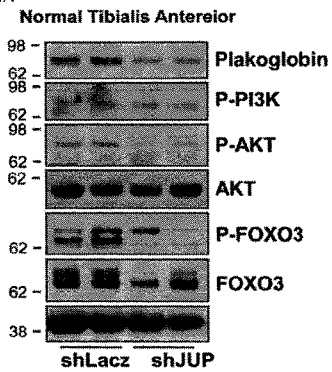
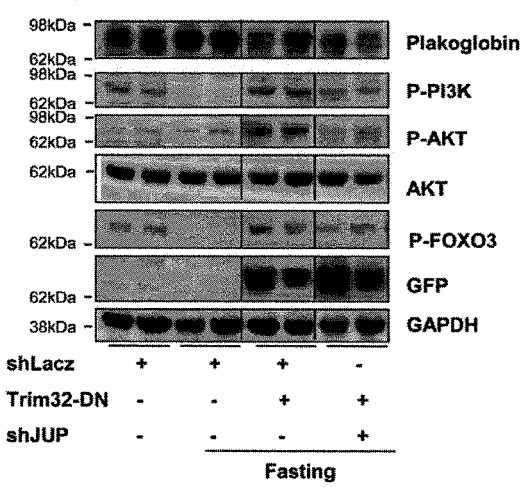
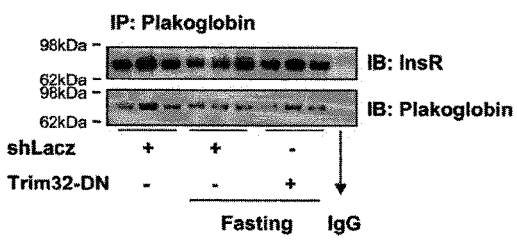
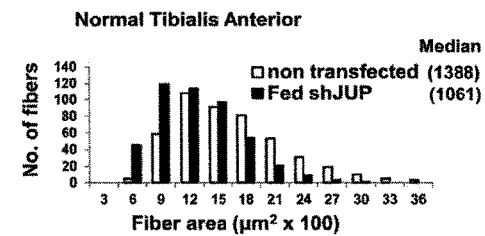
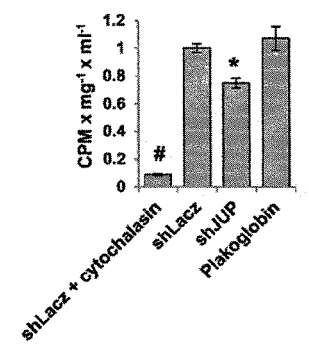
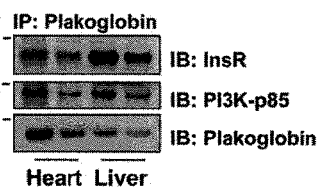
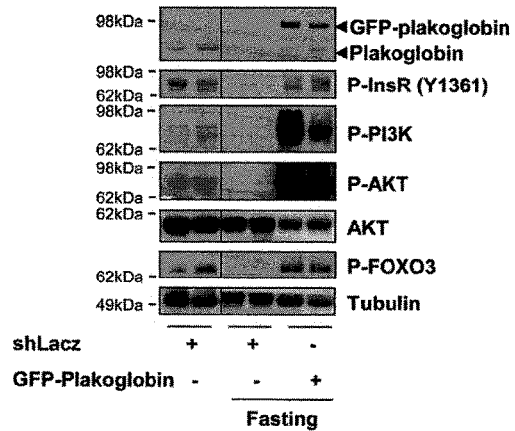

FIG. 5A
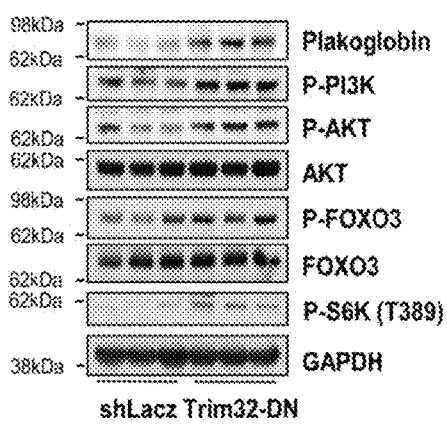
FIG. 5B Glucose uptake by C2C12 myoblasts
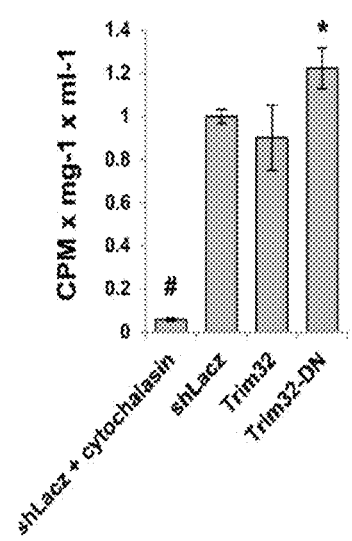

SEQUENCE LISTING

<160> NUMBER OF SEQ ID NOS: 21

<210> SEQ ID NO 1
<211> LENGTH: 655
<212> TYPE: PRT
<213> ORGANISM: Homo sapiens

<400> SEQUENCE: 1

```
Met Ala Ala Ala Ala Ala Ser His Leu Asn Leu Asp Ala Leu Arg
1               5                   10                  15

Glu Val Leu Glu Cys Pro Ile Cys Met Glu Ser Phe Thr Glu Glu Gln
            20                  25                  30

Leu Arg Pro Lys Leu Leu His Cys Gly His Thr Ile Cys Arg Gln Cys
        35                  40                  45

Leu Glu Lys Leu Leu Ala Ser Ser Ile Asn Gly Val Arg Cys Pro Phe
    50                  55                  60

Cys Ser Lys Ile Thr Arg Ile Thr Ser Leu Thr Gln Leu Thr Asp Asn
65                  70                  75                  80

Leu Thr Val Leu Lys Ile Ile Asp Thr Ala Gly Leu Ser Glu Ala Val
                85                  90                  95

Gly Leu Leu Met Cys Arg Gly Cys Gly Arg Arg Leu Pro Arg Gln Phe
            100                 105                 110

Cys Arg Ser Cys Gly Val Val Leu Cys Glu Pro Cys Arg Glu Ala Asp
        115                 120                 125

His Gln Pro Pro Gly His Cys Thr Leu Pro Val Lys Glu Ala Ala Glu
    130                 135                 140

Glu Arg Arg Arg Asp Phe Gly Glu Lys Leu Thr Arg Leu Arg Glu Leu
145                 150                 155                 160

Thr Gly Glu Leu Gln Arg Arg Lys Ala Ala Leu Glu Gly Val Ser Arg
                165                 170                 175

Asp Leu Gln Ala Arg Tyr Lys Ala Val Leu Gln Glu Tyr Gly His Glu
            180                 185                 190

Glu Arg Arg Ile Gln Glu Glu Leu Ala Arg Ser Arg Lys Phe Phe Thr
        195                 200                 205
```

```
Gly Ser Leu Ala Glu Val Glu Lys Ser Asn Ser Gln Val Val Glu Glu
    210                 215                 220
Gln Ser Tyr Leu Leu Asn Ile Ala Glu Val Gln Ala Val Ser Arg Cys
225                 230                 235                 240
Asp Tyr Phe Leu Ala Lys Ile Lys Gln Ala Asp Val Ala Leu Leu Glu
                245                 250                 255
Glu Thr Ala Asp Glu Glu Pro Glu Leu Thr Ala Ser Leu Pro Arg
            260                 265                 270
Glu Leu Thr Leu Gln Asp Val Glu Leu Leu Lys Val Gly His Val Gly
            275                 280                 285
Pro Leu Gln Ile Gly Gln Ala Val Lys Lys Pro Arg Thr Val Asn Met
290                 295                 300
Glu Asp Ser Trp Ala Gly Glu Glu Gly Ala Ala Ser Ser Ala Ser Ala
305                 310                 315                 320
Ser Val Thr Phe Arg Glu Met Asp Met Ser Pro Glu Glu Val Ala Pro
                325                 330                 335
Ser Pro Arg Ala Ser Pro Ala Lys Gln Arg Ser Ser Glu Ala Ala Ser
                340                 345                 350
Gly Ile Gln Gln Cys Leu Phe Leu Lys Lys Met Gly Ala Lys Gly Ser
                355                 360                 365
Thr Pro Gly Met Phe Asn Leu Pro Val Ser Leu Tyr Val Thr Ser Gln
            370                 375                 380
Ser Glu Val Leu Val Ala Asp Arg Gly Asn Tyr Arg Ile Gln Val Phe
385                 390                 395                 400
Asn Arg Lys Gly Phe Leu Lys Glu Ile Arg Arg Ser Pro Ser Gly Ile
                405                 410                 415
Asp Ser Phe Val Leu Ser Phe Leu Gly Ala Asp Leu Pro Asn Leu Thr
                420                 425                 430
Pro Leu Ser Val Ala Met Asn Cys His Gly Leu Ile Gly Val Thr Asp
            435                 440                 445
Ser Tyr Asp Asn Ser Leu Lys Val Tyr Thr Met Asp Gly His Cys Val
    450                 455                 460
Ala Cys His Arg Ser Gln Leu Ser Lys Pro Trp Gly Ile Thr Ala Leu
465                 470                 475                 480
Pro Ser Gly Gln Phe Val Val Thr Asp Val Glu Gly Gly Lys Leu Trp
                485                 490                 495
Cys Phe Thr Val Asp Arg Gly Ala Gly Val Val Lys Tyr Ser Cys Leu
                500                 505                 510
Cys Ser Ala Val Arg Pro Lys Phe Val Thr Cys Asp Ala Glu Gly Thr
            515                 520                 525
Val Tyr Phe Thr Gln Gly Leu Gly Leu Asn Val Glu Asn Arg Gln Asn
    530                 535                 540
Glu His His Leu Glu Gly Gly Phe Ser Ile Gly Ser Val Gly Pro Asp
545                 550                 555                 560
Gly Gln Leu Gly Arg Gln Ile Ser His Phe Ser Glu Asn Glu Asp
                565                 570                 575
Phe Arg Cys Ile Ala Gly Met Cys Val Asp Ala Arg Gly Asp Leu Ile
                580                 585                 590
Val Ala Asp Ser Ser Arg Lys Glu Ile Leu His Phe Pro Lys Gly Gly
            595                 600                 605
Gly Tyr Ser Val Leu Ile Arg Glu Gly Leu Thr Cys Pro Val Gly Ile
    610                 615                 620
```

```
Ala Leu Thr Pro Lys Gly Gln Leu Leu Val Leu Asp Cys Trp Asp His
625                 630                 635                 640

Cys Val Lys Ile Tyr Ser Tyr His Leu Arg Arg Tyr Ser Thr Pro
            645                 650                 655
```

<210> SEQ ID NO 2
<211> LENGTH: 609
<212> TYPE: PRT
<213> ORGANISM: Artificial Sequence
<220> FEATURE:
<223> OTHER INFORMATION: Trim32 Dominant Negative

<400> SEQUENCE: 2

```
Met Ala Ala Ala Ala Ala Ser His Leu Asn Leu Asp Ala Leu Arg
1               5                   10                  15

Glu Val Leu Ser Lys Ile Thr Arg Ile Thr Gly Leu Thr Gln Leu Thr
                20                  25                  30

Asp Asn Leu Thr Val Leu Lys Ile Ile Asp Thr Ala Gly Leu Ser Glu
            35                  40                  45

Ala Val Gly Leu Leu Met Cys Arg Gly Cys Gly Arg Arg Leu Pro Arg
    50                  55                  60

Gln Phe Cys Arg Ser Cys Gly Val Val Leu Cys Glu Pro Cys Arg Glu
65                  70                  75                  80

Ala Asp His Gln Pro Pro Gly His Cys Thr Leu Pro Val Lys Glu Ala
                85                  90                  95

Ala Glu Glu Arg Arg Arg Asp Phe Gly Glu Lys Leu Thr Arg Leu Arg
            100                 105                 110

Glu Leu Thr Gly Glu Leu Gln Arg Arg Lys Ala Ala Leu Glu Gly Val
        115                 120                 125

Ser Arg Asp Leu Gln Ala Arg Tyr Lys Ala Val Leu Gln Glu Tyr Gly
130                 135                 140

His Glu Glu Arg Arg Ile Gln Glu Glu Leu Ala Arg Ser Arg Lys Phe
145                 150                 155                 160

Phe Thr Gly Ser Leu Ala Glu Val Glu Lys Ser Asn Ser Gln Val Val
                165                 170                 175

Glu Glu Gln Ser Tyr Leu Leu Asn Ile Ala Glu Val Gln Ala Val Ser
            180                 185                 190

Arg Cys Asp Tyr Phe Leu Ala Lys Ile Lys Gln Ala Asp Val Ala Leu
        195                 200                 205

Leu Glu Glu Thr Ala Asp Glu Glu Pro Glu Leu Thr Ala Ser Leu
    210                 215                 220

Pro Arg Glu Leu Thr Leu Gln Asp Val Glu Leu Leu Lys Val Gly His
225                 230                 235                 240

Val Gly Pro Leu Gln Ile Gly Gln Ala Val Lys Lys Pro Arg Thr Val
                245                 250                 255

Asn Met Glu Asp Ser Trp Ala Gly Glu Glu Gly Ala Ala Ser Ser Ala
            260                 265                 270

Ser Ala Ser Val Thr Phe Arg Glu Met Asp Met Ser Pro Glu Glu Val
        275                 280                 285

Ala Pro Ser Pro Arg Ala Ser Pro Ala Lys Gln Arg Ser Ser Glu Ala
    290                 295                 300

Ala Ser Gly Ile Gln Gln Cys Leu Phe Leu Lys Lys Met Gly Ala Lys
305                 310                 315                 320

Gly Ser Thr Pro Gly Met Phe Asn Leu Pro Val Ser Leu Tyr Val Thr
                325                 330                 335
```

-continued

Ser Gln Ser Glu Val Leu Val Ala Asp Arg Gly Asn Tyr Arg Ile Gln
                340                 345                 350

Val Phe Asn Arg Lys Gly Phe Leu Lys Glu Ile Arg Arg Ser Pro Ser
        355                 360                 365

Gly Ile Asp Ser Phe Val Leu Ser Phe Leu Gly Ala Asp Leu Pro Asn
    370                 375                 380

Leu Thr Pro Leu Ser Val Ala Met Asn Cys His Gly Leu Ile Gly Val
385                 390                 395                 400

Thr Asp Ser Tyr Asp Asn Ser Leu Lys Val Tyr Thr Met Asp Gly His
                405                 410                 415

Cys Val Ala Cys His Arg Ser Gln Leu Ser Lys Pro Trp Gly Ile Thr
        420                 425                 430

Ala Leu Pro Ser Gly Gln Phe Val Thr Asp Val Glu Gly Gly Lys
    435                 440                 445

Leu Trp Cys Phe Thr Val Asp Arg Gly Ala Gly Val Val Lys Tyr Ser
    450                 455                 460

Cys Leu Cys Ser Ala Val Arg Pro Lys Phe Val Thr Cys Asp Ala Glu
465                 470                 475                 480

Gly Thr Val Tyr Phe Thr Gln Gly Leu Gly Leu Asn Val Glu Asn Arg
                485                 490                 495

Gln Asn Glu His His Leu Glu Gly Gly Phe Ser Ile Gly Ser Val Gly
        500                 505                 510

Pro Asp Gly Gln Leu Gly Arg Gln Ile Ser His Phe Ser Glu Asn
    515                 520                 525

Glu Asp Phe Arg Cys Ile Ala Gly Met Cys Val Asp Ala Arg Gly Asp
    530                 535                 540

Leu Ile Val Ala Asp Ser Ser Arg Lys Glu Ile Leu His Phe Pro Lys
545                 550                 555                 560

Gly Gly Gly Tyr Ser Val Leu Ile Arg Glu Gly Leu Thr Cys Pro Val
                565                 570                 575

Gly Ile Ala Leu Thr Pro Lys Gly Gln Leu Leu Val Leu Asp Cys Trp
        580                 585                 590

Asp His Cys Val Lys Ile Tyr Ser Tyr His Leu Arg Arg Tyr Ser Thr
    595                 600                 605

Pro

<210> SEQ ID NO 3
<211> LENGTH: 745
<212> TYPE: PRT
<213> ORGANISM: Homo sapiens

<400> SEQUENCE: 3

Met Glu Val Met Asn Leu Ile Glu Gln Pro Ile Lys Val Thr Glu Trp
1               5                   10                  15

Gln Gln Thr Tyr Thr Tyr Asp Ser Gly Ile His Ser Gly Val Asn Thr
                20                  25                  30

Cys Val Pro Ser Val Ser Ser Lys Gly Ile Met Asp Glu Asp Ala
        35                  40                  45

Cys Gly Arg Gln Tyr Thr Leu Lys Lys Thr Thr Tyr Thr Gln Gly
    50                  55                  60

Val Pro Gln Asn Gln Gly Asp Leu Glu Tyr Gln Met Ser Thr Thr Ala
65                  70                  75                  80

Arg Ala Lys Arg Val Arg Glu Ala Met Cys Pro Gly Val Ser Gly Glu
                85                  90                  95

```
Asp Ser Ser Leu Leu Leu Ala Thr Gln Val Glu Gly Gln Thr Thr Asn
            100                 105                 110

Leu Gln Arg Leu Ala Glu Pro Ser Gln Leu Leu Lys Ser Ala Ile Val
        115                 120                 125

His Leu Ile Asn Tyr Gln Asp Asp Ala Glu Leu Ala Thr Arg Ala Leu
    130                 135                 140

Pro Glu Leu Thr Lys Leu Leu Asn Asp Glu Asp Pro Val Val Val Thr
145                 150                 155                 160

Lys Ala Ala Met Ile Val Asn Gln Leu Ser Lys Lys Glu Ala Ser Arg
                165                 170                 175

Arg Ala Leu Met Gly Ser Pro Gln Leu Val Ala Ala Val Val Arg Thr
            180                 185                 190

Met Gln Asn Thr Ser Asp Leu Asp Thr Ala Arg Cys Thr Thr Ser Ile
        195                 200                 205

Leu His Asn Leu Ser His His Arg Glu Gly Leu Leu Ala Ile Phe Lys
    210                 215                 220

Ser Gly Gly Ile Pro Ala Leu Val Arg Met Leu Ser Ser Pro Val Glu
225                 230                 235                 240

Ser Val Leu Phe Tyr Ala Ile Thr Thr Leu His Asn Leu Leu Leu Tyr
                245                 250                 255

Gln Glu Gly Ala Lys Met Ala Val Arg Leu Ala Asp Gly Leu Gln Lys
            260                 265                 270

Met Val Pro Leu Leu Asn Lys Asn Asn Pro Lys Phe Leu Ala Ile Thr
        275                 280                 285

Thr Asp Cys Leu Gln Leu Leu Ala Tyr Gly Asn Gln Glu Ser Lys Leu
    290                 295                 300

Ile Ile Leu Ala Asn Gly Gly Pro Gln Gly Leu Val Gln Ile Met Arg
305                 310                 315                 320

Asn Tyr Ser Tyr Glu Lys Leu Leu Trp Thr Thr Ser Arg Val Leu Lys
                325                 330                 335

Val Leu Ser Val Cys Pro Ser Asn Lys Pro Ala Ile Val Glu Ala Gly
            340                 345                 350

Gly Met Gln Ala Leu Gly Lys His Leu Thr Ser Asn Ser Pro Arg Leu
        355                 360                 365

Val Gln Asn Cys Leu Trp Thr Leu Arg Asn Leu Ser Asp Val Ala Thr
    370                 375                 380

Lys Gln Glu Gly Leu Glu Ser Val Leu Lys Ile Leu Val Asn Gln Leu
385                 390                 395                 400

Ser Val Asp Asp Val Asn Val Leu Thr Cys Ala Thr Gly Thr Leu Ser
                405                 410                 415

Asn Leu Thr Cys Asn Asn Ser Lys Asn Lys Thr Leu Val Thr Gln Asn
            420                 425                 430

Ser Gly Val Glu Ala Leu Ile His Ala Ile Leu Arg Ala Gly Asp Lys
        435                 440                 445

Asp Asp Ile Thr Glu Pro Ala Val Cys Ala Leu Arg His Leu Thr Ser
    450                 455                 460

Arg His Pro Glu Ala Glu Met Ala Gln Asn Ser Val Arg Leu Asn Tyr
465                 470                 475                 480

Gly Ile Pro Ala Ile Val Lys Leu Leu Asn Gln Pro Asn Gln Trp Pro
                485                 490                 495

Leu Val Lys Ala Thr Ile Gly Leu Ile Arg Asn Leu Ala Leu Cys Pro
            500                 505                 510

Ala Asn His Ala Pro Leu Gln Glu Ala Ala Val Ile Pro Arg Leu Val
```

```
            515                 520                 525
Gln Leu Leu Val Lys Ala His Gln Asp Ala Gln Arg His Val Ala Ala
    530                 535                 540
Gly Thr Gln Gln Pro Tyr Thr Asp Gly Val Arg Met Glu Glu Ile Val
545                 550                 555                 560
Glu Gly Cys Thr Gly Ala Leu His Ile Leu Ala Arg Asp Pro Met Asn
                565                 570                 575
Arg Met Glu Ile Phe Arg Leu Asn Thr Ile Pro Leu Phe Val Gln Leu
            580                 585                 590
Leu Tyr Ser Ser Val Glu Asn Ile Gln Arg Val Ala Ala Gly Val Leu
        595                 600                 605
Cys Glu Leu Ala Gln Asp Lys Glu Ala Ala Asp Ala Ile Asp Ala Glu
    610                 615                 620
Gly Ala Ser Ala Pro Leu Met Glu Leu Leu His Ser Arg Asn Glu Gly
625                 630                 635                 640
Thr Ala Thr Tyr Ala Ala Ala Val Leu Phe Arg Ile Ser Glu Asp Lys
                645                 650                 655
Asn Pro Asp Tyr Arg Lys Arg Val Ser Val Glu Leu Thr Asn Ser Leu
            660                 665                 670
Phe Lys His Asp Pro Ala Ala Trp Glu Ala Ala Gln Ser Met Ile Pro
        675                 680                 685
Ile Asn Glu Pro Tyr Ala Asp Asp Met Asp Ala Thr Tyr Arg Pro Met
    690                 695                 700
Tyr Ser Ser Asp Val Pro Leu Asp Pro Leu Asp Met His Met Asp Leu
705                 710                 715                 720
Asp Gly Asp Tyr Pro Met Asp Thr Tyr Ser Asp Gly Leu Arg Pro Pro
                725                 730                 735
Tyr Pro Thr Ala Asp His Met Leu Ala
            740                 745

<210> SEQ ID NO 4
<211> LENGTH: 1057
<212> TYPE: DNA
<213> ORGANISM: Artificial Sequence
<220> FEATURE:
<223> OTHER INFORMATION: Trim32 Dominant Negative
<220> FEATURE:
<221> NAME/KEY: misc_feature
<222> LOCATION: (649)..(649)
<223> OTHER INFORMATION: n is a, c, g, or t
<220> FEATURE:
<221> NAME/KEY: misc_feature
<222> LOCATION: (662)..(662)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (811)..(811)
<223> OTHER INFORMATION: n is a, c, g, or t
<220> FEATURE:
<221> NAME/KEY: misc_feature
<222> LOCATION: (835)..(835)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
```

-continued

```
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
<220> FEATURE:
<221> NAME/KEY: misc_feature
<222> LOCATION: (867)..(868)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (884)..(885)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t
<220> FEATURE:
<221> NAME/KEY: misc_feature
<222> LOCATION: (928)..(928)
<223> OTHER INFORMATION: n is a, c, g, or t
<220> FEATURE:
<221> NAME/KEY: misc_feature
<222> LOCATION: (938)..(938)
<223> OTHER INFORMATION: n is a, c, g, or t
<220> FEATURE:
<221> NAME/KEY: misc_feature
<222> LOCATION: (950)..(950)
<223> OTHER INFORMATION: n is a, c, g, or t
<220> FEATURE:
<221> NAME/KEY: misc_feature
<222> LOCATION: (974)..(974)
<223> OTHER INFORMATION: n is a, c, g, or t
<220> FEATURE:
<221> NAME/KEY: misc_feature
<222> LOCATION: (977)..(980)
<223> OTHER INFORMATION: n is a, c, g, or t
<220> FEATURE:
<221> NAME/KEY: misc_feature
<222> LOCATION: (986)..(986)
<223> OTHER INFORMATION: n is a, c, g, or t
<220> FEATURE:
<221> NAME/KEY: misc_feature
<222> LOCATION: (992)..(993)
<223> OTHER INFORMATION: n is a, c, g, or t
<220> FEATURE:
<221> NAME/KEY: misc_feature
<222> LOCATION: (1002)..(1002)
<223> OTHER INFORMATION: n is a, c, g, or t
<220> FEATURE:
<221> NAME/KEY: misc_feature
<222> LOCATION: (1006)..(1006)
<223> OTHER INFORMATION: n is a, c, g, or t
<220> FEATURE:
<221> NAME/KEY: misc_feature
<222> LOCATION: (1009)..(1010)
<223> OTHER INFORMATION: n is a, c, g, or t
<220> FEATURE:
<221> NAME/KEY: misc_feature
<222> LOCATION: (1014)..(1015)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1027)..(1028)
```

<223> OTHER INFORMATION: n is a, c, g, or t
<220> FEATURE:
<221> NAME/KEY: misc_feature
<222> LOCATION: (1030)..(1030)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1036)..(1036)
<223> OTHER INFORMATION: n is a, c, g, or t
<220> FEATURE:
<221> NAME/KEY: misc_feature
<222> LOCATION: (1042)..(1042)
<223> OTHER INFORMATION: n is a, c, g, or t
<220> FEATURE:
<221> NAME/KEY: misc_feature
<222> LOCATION: (1044)..(1045)
<223> OTHER INFORMATION: n is a, c, g, or t
<220> FEATURE:
<221> NAME/KEY: misc_feature
<222> LOCATION: (1048)..(1049)
<223> OTHER INFORMATION: n is a, c, g, or t

<400> SEQUENCE: 4
acgccgccgc catcactctc ggcatggacg agctgtacaa gtccggactc agatctcgag      60
aattctgccg aggctgtggt gtggtgttgt gtgaaccctg ccgggaggca gatcaccaac     120
cccctggcca ctgcacactt ccggtcaagg aggcagctga ggagcggcgg agggacttcg     180
gggagaagtt gactcgtcta agggaactta ctggagagct gcagaggagg aaggtagcct     240
tggagggcgt ctccagggat cttcaggcaa ggtataaggc tgttcttcaa gaatatggcc     300
atgaggaacg ccgcatccag gaagagctag cccgctctcg gaagttcttc acaggctcct     360
tggctgaggt tgagaagtcc aacagtcaag tggtagagga gcagagctac ctactcaaca     420
ttgctgaggt gcaggccgtg tctcgctgtg actactttct agcgaagatc aagcaagctg     480
atgtagccct cctggaggag acagcggatg aggaggagcc cgagctcact gccagcctac     540
cccgggagct taccctgcaa gatgtggagc tccttaaggt aggacacgtt ggtcctctgc     600
aaattggcca ggctgttaag aagccccgga cagttaacat ggaagattnc tgggcagggg     660
angagggganc agcatcttct gcctcagcct cggtaacctt tagagagatg gacatgagcc     720
ctgaggaata acttcccacc cctanggctt ccccgcgaaa cacggagttc ttgaggcagc     780
ttccggtatc caacagtgtc tgtttctcaa naaaatgggg gcgaaaggca accanttccc     840
ggcantggtt caatcnttcc antccannct tctntgggaa cnannccaaa atggangggg     900
ttggtttgcc caccggggca aattttcnaa tcccaagngg ttcaacccnn aaagggtttt     960
tttaagggaa atcnccnnnn ccccncgggg gnnttgaaaa cnttcnggnn aaanntccc    1020
ttngggnncn anttgnccaa antnnccnnc ccttttt                             1057

<210> SEQ ID NO 5
<211> LENGTH: 21
<212> TYPE: DNA
<213> ORGANISM: Artificial Sequence
<220> FEATURE:
<223> OTHER INFORMATION: SHRNA Trim32-1

<400> SEQUENCE: 5
ggctgattgg tgtcactgat a                                                21

<210> SEQ ID NO 6
<211> LENGTH: 21

<212> TYPE: DNA
<213> ORGANISM: Artificial Sequence
<220> FEATURE:
<223> OTHER INFORMATION: SHRNA Trim32-2

<400> SEQUENCE: 6
agctgctggt cttggactgt t                                              21

<210> SEQ ID NO 7
<211> LENGTH: 21
<212> TYPE: DNA
<213> ORGANISM: Artificial Sequence
<220> FEATURE:
<223> OTHER INFORMATION: SHLACZ

<400> SEQUENCE: 7
aaatcgctga tttgtgtagt c                                              21

<210> SEQ ID NO 8
<211> LENGTH: 21
<212> TYPE: DNA
<213> ORGANISM: Artificial Sequence
<220> FEATURE:
<223> OTHER INFORMATION: Trim32 shRNA 1

<400> SEQUENCE: 8
ggctgattgg tgtcactgat a                                              21

<210> SEQ ID NO 9
<211> LENGTH: 21
<212> TYPE: DNA
<213> ORGANISM: Artificial Sequence
<220> FEATURE:
<223> OTHER INFORMATION: shRNA 2 Trim32

<400> SEQUENCE: 9
agctgctggt cttggactgt t                                              21

<210> SEQ ID NO 10
<211> LENGTH: 21
<212> TYPE: DNA
<213> ORGANISM: Artificial Sequence
<220> FEATURE:
<223> OTHER INFORMATION: shRNA Plakoglobin

<400> SEQUENCE: 10
ggaactacag ctacgagaag c                                              21

<210> SEQ ID NO 11
<211> LENGTH: 21
<212> TYPE: DNA
<213> ORGANISM: Artificial Sequence
<220> FEATURE:
<223> OTHER INFORMATION: shRNA Plakoglobin

<400> SEQUENCE: 11
gggcatcatg gatgaggatg a                                              21

<210> SEQ ID NO 12
<211> LENGTH: 21
<212> TYPE: DNA
<213> ORGANISM: Artificial Sequence
<220> FEATURE:
<223> OTHER INFORMATION: shRNA Desmoplakin

<400> SEQUENCE: 12

```
agaccggaaa catcatctct t                                          21

<210> SEQ ID NO 13
<211> LENGTH: 21
<212> TYPE: DNA
<213> ORGANISM: Artificial Sequence
<220> FEATURE:
<223> OTHER INFORMATION: shRNA Desmoplakin

<400> SEQUENCE: 13
caaagagaaa tggcttccct a                                          21

<210> SEQ ID NO 14
<211> LENGTH: 20
<212> TYPE: DNA
<213> ORGANISM: Artificial Sequence
<220> FEATURE:
<223> OTHER INFORMATION: qPCR primer Forward Atrogin1

<400> SEQUENCE: 14
tgggtgtatc ggatggagac                                            20

<210> SEQ ID NO 15
<211> LENGTH: 20
<212> TYPE: DNA
<213> ORGANISM: Artificial Sequence
<220> FEATURE:
<223> OTHER INFORMATION: qPCR primer Reverse Atrogin1

<400> SEQUENCE: 15
tcagcctctg catgatgttc                                            20

<210> SEQ ID NO 16
<211> LENGTH: 20
<212> TYPE: DNA
<213> ORGANISM: Artificial Sequence
<220> FEATURE:
<223> OTHER INFORMATION: qPCR primer Forward MuRF1

<400> SEQUENCE: 16
gtccatgtct ggaggtcgtt                                            20

<210> SEQ ID NO 17
<211> LENGTH: 20
<212> TYPE: DNA
<213> ORGANISM: Artificial Sequence
<220> FEATURE:
<223> OTHER INFORMATION: qPCR primer Reverse MuRF1

<400> SEQUENCE: 17
aggagcaagt aggcacctca                                            20

<210> SEQ ID NO 18
<211> LENGTH: 20
<212> TYPE: DNA
<213> ORGANISM: Artificial Sequence
<220> FEATURE:
<223> OTHER INFORMATION: qPCR primer Forward GAPDH

<400> SEQUENCE: 18
acccagaaga ctgtggatgg                                            20

<210> SEQ ID NO 19
<211> LENGTH: 20
<212> TYPE: DNA
<213> ORGANISM: Artificial Sequence
```

```
<220> FEATURE:
<223> OTHER INFORMATION: qPCR primer Reverse GAPDH

<400> SEQUENCE: 19
cacattgggg gtaggaacac                                               20

<210> SEQ ID NO 20
<211> LENGTH: 20
<212> TYPE: DNA
<213> ORGANISM: Artificial Sequence
<220> FEATURE:
<223> OTHER INFORMATION: qPCR primer Forward Plakoglobin

<400> SEQUENCE: 20
ctgtgtgccc tctgtaagca                                               20

<210> SEQ ID NO 21
<211> LENGTH: 20
<212> TYPE: DNA
<213> ORGANISM: Artificial Sequence
<220> FEATURE:
<223> OTHER INFORMATION: qPCR primer Reverse Plakoglobin

<400> SEQUENCE: 21
gaactgtcct cgcctgagac                                               20
```

METHODS FOR INDUCING GLUCOSE UPTAKE

CROSS-REFERENCE TO RELATED APPLICATION

This application is a U.S. national phase of International Application No. PCT/IL2014/050810, filed Sep. 11, 2014, which claims priority to U.S. Provisional Application No. 61/876,929, filed Sep. 12, 2013, the disclosures of which are hereby incorporated by reference in their entirety.

FIELD OF INVENTION

This invention is directed to; inter alia, a method for inducing glucose uptake in a muscle cell by inhibiting Trim32 protein and/or increasing the abundance of plakoglobin in the muscle cell.

BACKGROUND OF THE INVENTION

Growth of skeletal and cardiac muscles, like that of dividing cells, is largely dependent on signaling through the Insulin/PI3K/Akt/FoxO pathway. Conversely, the atrophy of specific muscles upon disuse, wasting, or denervation and the systemic muscle wasting in fasting and disease states (e.g. cancer cachexia, sepsis, and untreated diabetes) results from reduced activity of this pathway. This rapid loss of muscle mass results primarily through accelerated degradation of myofibrillar and soluble proteins, but in most catabolic states (e.g. fasting), protein synthesis also decreases.

FoxO (forkhead box O) transcription factors, one of the main downstream mediators of PI3K (phosphatidylinositol-3 kinase)/Akt [also known as PKB (protein kinase B)] signal transduction pathway, play an important role in modulating cellular homoeostasis. Recent studies have revealed the significance of FoxO in bone, the interaction of FoxO with -catenin, along with mechanical stress-induced inactivation of FoxO via PI3K/Akt.

Development of these various types of atrophy requires the transcription of a common set of atrophy-related genes ("atrogenes") by FoxO transcription factors, whose activation is sufficient to cause accelerated proteolysis and atrophy. In atrophying muscles, multiple components of the ubiquitin-proteasome pathway (UPS), such as the muscle-specific ubiquitin ligases, MuRF1 and Atrogin1/MAFbx, are induced and their induction is essential for rapid wasting. Another ubiquitin ligase that appears to be critical for atrophy is Trim32. Like MuRF1, Trim32 contains a tripartite motif (RING; B-box; coiled-coil), but also has six NHL repeats with putative protein binding properties, and mutations in the third repeat causes Limb Girdle Muscular Dystrophy 2H. We demonstrated that during muscle wasting, MuRF1 is essential for the ubiquitin-dependent degradation of proteins comprising the thick filament, while Trim32 catalyzes the linked disassembly and degradation of the desmin cytoskeleton, Z-band, and thin filament proteins, which are linked processes.

SUMMARY OF THE INVENTION

In one embodiment, the present invention provides a method for inducing glucose uptake in a muscle cell, comprising the step of inhibiting Trim32 protein in said cell, thereby inducing glucose uptake in a muscle cell. In some embodiments, the cell is a skeletal muscle cell. In some embodiments, inducing glucose uptake in a muscle cell further includes muscle fiber growth. In some embodiments, inducing glucose uptake in a muscle cell is inducing the phosphorylation of insulin receptor in the cell.

In a further embodiment, the present invention provides a method for inducing glucose uptake in a muscle cell, comprising the step of increasing the abundance of plakoglobin protein in the cell, thereby inducing glucose uptake in a muscle cell. In some embodiments, the cell is a skeletal muscle cell. In some embodiments, the cell is a skeletal muscle cell. In some embodiments, increasing the abundance of plakoglobin protein in the cell results in muscle fiber growth. In some embodiments, increasing the abundance of plakoglobin protein in the cell results in inducing the phosphorylation of insulin receptor in the cell.

BRIEF DESCRIPTION OF THE DRAWINGS

FIG. 4. Plakoglobin downregulation reduces PI3K/Akt/FoxO signaling, glucose uptake and fiber size. (A) Is a gel micrograph showing that plakoglobin knockdown with shJUP results in reduced PI3K/Akt/FoxO signaling. Normal muscles were electroporated with shLacz or plakoglobin shRNA (shJUP), and soluble extracts were analyzed by SDS-PAGE, and immunoblot. (B) is a bar graph showing that downregulation of plakoglobin induces muscle atrophy. Cross sectional areas of 500 fibers transfected with shJUP (that express GFP) (black bars) vs. 500 non transfected fibers (open bars) in the same muscle. n=6. (C) Is a gel micrograph showing that during fasting, downregulation of plakoglobin reduces the increase in PI3K/Akt/FoxO signaling induced by Trim32-DN. Soluble fractions of muscles expressing shLacz alone, Trim32-DN together with shLacz, or Trim32-DN together with shJUP were analyzed by SDS-PAGE and immunoblot. (D) is a bar graph showing that plakoglobin downregulation in C2C12 myoblasts reduces insulin-induced glucose uptake. [3H]2-Deoxy-D-glucose uptake (cpm) was measured in C2C12 myoblasts expressing shLacz, shJUP or plakoglobin. To determine the insulin-dependent glucose uptake, the values measured in the presence of 20 μM cytochalasin B were subtracted from the total uptake. n=3, * p<0.05 vs. shLacz, # p<0.005 vs. shLacz. (E) Is a gel micrograph showing that in normal muscle and during fasting, plakoglobin is associated with insulin receptor. Plakoglobin was immunoprecipitated from the soluble fraction of muscles expressing shLacz or Trim32-DN from fed or fasted mice. Precipitates were analyzed by immunoblotting for plakoglobin or insulin receptor. (F) Is a gel micrograph showing that plakoglobin associates with insulin receptor in heart and liver. Plakoglobin was immunoprecipitated from the soluble fraction of heart and liver from fed mice and analyzed by immunoblotting. (G) Is a gel micrograph showing that during fasting, overexpression of plakoglobin alone activates insulin receptor and enhances PI3K/Akt/FoxO signaling. Soluble fractions of normal and atrophying muscles expressing shLacz or GFP-plakoglobin were analyzed by SDS-PAGE and immunoblot.

FIG. 5. Trim32 Inhibition in normal muscle increases PI3K/Akt/FoxO activity and glucose uptake. (A) is a micrograph showing that inhibition of Trim32 by Trim32-DN increases plakoglobin and PI3K/Akt/FoxO activity. Soluble fractions of normal TA muscles expressing shLacz or Trim32-DN were analyzed by SDS-PAGE and immunoblot. (B) is a bar graph showing that Trim32 inhibition in C2C12 myoblasts increases insulin-induced glucose uptake. [3H]2-Deoxy-D-glucose uptake was measured in C2C12 myoblasts expressing shLacz, Trim32 or Trim32-DN, as in FIG. 4D, n=3, * p<0.005 vs. shLacz, # p<0.005 vs. shLacz.

DETAILED DESCRIPTION OF THE INVENTION

Figure 1A:
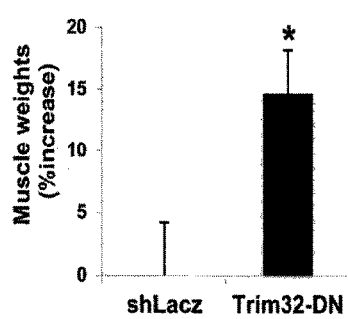
FIG. 1. Inhibition of Trim32 in normal muscle induces rapid growth. TA muscles were electroporated with shLacz or Trim32-DN and analyzed six days later. (A) a bar graph showing the mean weights of Trim32-DN expressing muscles are presented as percent increase versus control. n=10, * p<0.05. (B) a micrograph showing representative muscle cross sectional area, and a bar graph showing cross sectional areas of 500 fibers transfected with GFP-Trim32-DN (black vs. 500 non-transfected fibers (open) in the same muscle. n=6. Laminin staining is in red. Scale bar=15 μm.

In one embodiment, the present invention provides a method for inducing glucose uptake in a muscle cell, comprising the step of inhibiting Trim32 protein in the cell, thereby inducing glucose uptake in a muscle cell. In another embodiment, a muscle cell is a cell within an atrophying muscle. In another embodiment, a muscle cell is a cell within a muscle exposed to fasting conditions. In another embodiment, a muscle cell is a cell of a subject afflicted with diabetes. In another embodiment, a muscle cell is a cell of a subject afflicted with type I diabetes. In another embodiment, a muscle cell is a cell of a subject afflicted with type II diabetes.

In another embodiment, a Trim32 protein of the invention comprises or consists the amino acid sequence: MAAAAAASHLNLDALREVLECPICMESFTEEQLRP-KLLHCGHTICRQCLEKLLASSINGV RCPFCSKITRIT-SLTQLTDNLTVLKIIDTAGLSEAVGLLMCRGCGRRL-PRQFCRSCGVVLC EPCREADHQPPGHCTLPVKE-AAEERRRDFGEKLTRLRELTGELQRRKAALEG-VSRDLQA RYKAVLQEYGHEERRIQEELARSRKFFTG-SLAEVEKSNSQVVEEQSYLLNIAEVQAVSRC DYFL-AKIKQADVALLEETADEEEPELTASLPRELTLQD-VELLKVGHVGPLQIGQAVKKPR TVNMEDSWAGEE-GAASSASASVTFREMDMSPEEVAPSPRASPAKQRS-SEAASGIQQCLF LKKMGAKGSTPGMFNLPVS-LYVTSQSEVLVADRGNYRIQVFNRKGFLKEIRRSPS-GIDSF VLSFLGADLPNLTPLSVAMNCHGLIGVTD-SYDNSLKVYTMDGHCVACHRSQLSKPWGIT ALPS-GQFVVTDVEGGKLWCFTVDRGAGVVKYSCLCSAV-RPKFVTCDAEGTVYFTQGLG LNVENRQNEHHLEG-GFSIGSVGPDGQLGRQISHFFSENEDFRCIAGMCV-DARGDLIVADS SRKEILHFPKGGGYSVLIREGLTCPV-GIALTPKGQLLVLDCWDHCVKIYSYHLRRYSTP (SEQ ID NO: 1). In another embodiment, a Trim32 protein is a fragment of SEQ ID NO: 1 having a Trim32 protein activity as described herein. In another embodiment, a Trim32 protein is a mutant of SEQ ID NO: 1 having a Trim32 protein activity as described herein.

In another embodiment, inducing glucose uptake is enhancing glucose uptake. In another embodiment, inducing glucose uptake is increasing glucose uptake. In another embodiment, inducing glucose uptake is increasing the concentration of glucose within a muscle cell. In another embodiment, inducing glucose uptake is increasing intracellular glucose by at least 20%. In another embodiment, inducing glucose uptake is increasing intracellular glucose by at least 30%. In another embodiment, inducing glucose uptake is increasing intracellular glucose by at least 40%. In another embodiment, inducing glucose uptake is increasing intracellular glucose by at least 50%. In another embodiment, inducing glucose uptake is increasing intracellular glucose by at least 1.5 folds. In another embodiment, inducing glucose uptake is increasing intracellular glucose by at least 2 folds. In another embodiment, inducing glucose uptake is increasing intracellular glucose by at least 3 folds. In another embodiment, inducing glucose uptake is increasing intracellular glucose by at least 4 folds. In another embodiment, inducing glucose uptake is increasing intracellular glucose by at least 5 folds. In another embodiment, inducing glucose uptake is increasing intracellular glucose by at least 10 folds.

In another embodiment, inhibiting Trim32 protein is inhibiting the activity of the Trim32 protein. In another embodiment, inhibiting Trim32 protein is inhibiting the translation of the mRNA molecule encoding Trim32 protein. In another embodiment, inhibiting Trim32 protein is inhibiting the transcription of Trim32 mRNA. In another embodiment, a synthetic mRNA molecule encodes a dominant negative Trim 32 protein. In another embodiment, a synthetic mRNA molecule comprises a 5-methylcytidine base, a pseudouridine base, or a combination thereof.

In another embodiment, inhibiting Trim32 protein is contacting a muscle cell with an antisense oligonucleotide (AS-ODNs) directed against Trim32. In another embodiment, inhibiting Trim32 protein is contacting a muscle cell with a ribozyme directed against Trim32. In another embodiment, inhibiting Trim32 protein is contacting a muscle cell with a small interfering RNAs (siRNAs) directed against Trim32. In another embodiment, inhibiting Trim32 protein is contacting a muscle cell with a RNA interference (RNAi) molecule directed against Trim32. In another embodiment, inhibiting Trim32 protein is contacting a muscle cell with an antagomir antisense directed against Trim32. In another embodiment, inhibiting Trim32 protein is contacting a muscle cell with a microRNA designed to silence Trim32.

In another embodiment, inhibiting Trim32 protein is contacting a muscle cell with a mutant protein Trim32 protein lacking Trim 32 activity. In another embodiment, inhibiting Trim32 protein is contacting a muscle cell with a dominant negative (DN) Trim32 protein. In another embodiment, a dominant negative (DN) Trim32 protein of the invention comprises or consists the amino acid sequence: MAAAAAASHLNLDALREVLSKITRITGLTQLTDNLT-VLKIIDTAGLSEAVGLLMCRGCGR RLPRQFCRSCGV-VLCEPCREADHQPPGHCTLPVKEAAEERRRDFGEKL-TRLRELTGELQR RKAALEGVSRDLQARYKAVL-QEYGHEERRIQEELARSRKFFTGSLAEVEKSNSQV-VEEQ SYLLNIAEVQAVSRCDYFLAKIKQAD-VALLEETADEEEPELTASLPRELTLQDVELLKVG HVGPLQIGQAVKKPRTVNMEDSWAGEEGAASSAS-ASVTFREMDMSPEEVAPSPRASPAK QRSSEAAS-GIQQCLFLKKMGAKGSTPGMFNLPVSLYVTSQSEVL-VADRGNYRIQVFNRK GFLKEIRRSPSGIDSFVLSF-LGADLPNLTPLSVAMNCHGLIGVTDSYDNSLKVYT-MDGHC VACHRSQLSKPWGITALPSGQFVVTDVEGG-KLWCFTVDRGAGVVKYSCLCSAVRPKFV TCDAEGT-VYFTQGLGLNVENRQNEHHLEGGFSIGSVGPDGQL-GRQISHFFSENEDFRCIA GMCVDARGDLIVADSS-RKEILHFPKGGGYSVLIREGLTCPVGIALTPKGQLLV-LDCWDHC VKIYSYHLRRYSTP (SEQ ID NO: 2). In another embodiment, a DN Trim32 protein is a fragment of SEQ ID NO: 2 having a DN Trim32 protein activity as described herein. In another embodiment, a DN Trim32 protein is a mutant of SEQ ID NO: 2 having a Trim32 protein activity as described herein. In another embodiment, a DN Trim32 protein is a fragment of SEQ ID NO: 1 which abolishes a Trim32 protein activity as described herein. In another embodiment, a DN Trim32 protein is a mutant of SEQ ID NO: 1 which abolishes a Trim32 protein activity as described herein.

In another embodiment, a dominant negative (DN) Trim32 protein of the invention is encoded by a DNA sequence which comprises or consists the nucleic acid sequence: ACGCCGCCGCCATCACTCTCGGCATGGAC-GAGCTGTACAAGTCCGGACTCAGATCTC GAGAAT-TCTGCCGAGGCTGTGGTGTGGTGTTGTGTGAAC-CCTGCCGGGAGGCAGATC ACCAACCCCCTGGCC-ACTGCACACTTCCGGTCAAGGAGGCAGCTGAG-GAGCGGCGG AGGGACTTCGGGGAGAAGTTGACT-CGTCTAAGGGAACTTACTGGAGAGCTGCAGAG GAGGAAGGTAGCCTTGGAGGGCGTCTCCAGGGA-TCTTCAGGCAAGGTATAAGGCTGT TCTTCAA-GAATATGGCCATGAGGAACGCCGCATCCAGGAA-GAGCTAGCCCGCTCTCG GAAGTTCTTCACAG-GCTCCTTGGCTGAGGTTGAGAAGTCCAACAGT-CAAGTGGTAGA GGAGCAGAGCTACCTACT-CAACATTGCTGAGGTGCAGGCCGTGTCTCGCTGT-GACTA CTTTCTAGCGAAGATCAAGCAAGCTGATG-TAGCCCTCCTGGAGGAGACAGCGGATGA GGAG-GAGCCCGAGCTCACTGCCAGCCTACCCCG-GGAGCTTACCCTGCAAGATGTGGA GCTCCT-TAAGGTAGGACACGTTGGTCCTCTGCAAATTGGC-CAGGCTGTTAAGAAGCC CCGGACAGTTAACATG-GAAGATTNCTGGGCAGGGGANGAGGGANCAGCA-TCTTCTG CCTCAGCCTCGGTAACCTTTAGAGA-GATGGACATGAGCCCTGAGGAATAACTTCCCA CCCCTANGGCTTCCCCGCGAAACACGGAGTTCTT-GAGGCAGCTTCCGGTATCCAACA GTGTCTGTTTCT-CAANAAAATGGGGGCGAAAGGCAACCANTTCCCG-GCANTGGTTCA ATCNTTCCANTCCANNCTTCT-NTGGGAACNANNCCAAAATGGANGGGGTTG-GTTTGC CCACCGGGGCAAATTTTCNAATC-CCAAGNGGTTCAACCCCNAAAGGGTTTTTTAAG GGAAATCNCCNNNNCCCCCNGGGGGNNTT-GAAAACNTTCNGGNNAAANNTTCCCTT NGGGNNCNANTTGNCCAAANTNNCCNNCCCTTTTT (SEQ ID NO: 4).

In another embodiment, inhibiting Trim32 protein is contacting a muscle cell with a mutant protein Trim32 protein lacking Trim 32 muscle activity. In another embodiment, inhibiting Trim32 protein is contacting a muscle cell with a small molecule that abolishes Trim32 muscle activity. In another embodiment, inhibiting Trim32 protein is contacting a muscle cell with a Trim32 competitive inhibitor. In another embodiment, inhibiting Trim32 protein is contacting a muscle cell with a Trim32 antibody which renders Trim32 protein-inactive. In another embodiment, the antibody is a polyclonal antibody. In another embodiment, the antibody is a monoclonal antibody. In another embodiment, the antibody is a single-chain variable fragment (scFv) directed against the Trim32 protein.

In another embodiment, inhibiting Trim32 protein in a muscle cell according to the present invention results in increase in the concentration of plakoglobin in a muscle cell. In another embodiment, inhibiting Trim32 protein in a muscle cell according to the present invention results in the induction of insulin receptor. In another embodiment, inhibiting Trim32 protein in a muscle cell according to the present invention results in the induction of phosphorylation of insulin receptor in the cell. In another embodiment, inhibiting Trim32 protein in a muscle cell according to the present invention results in increase of PI3K/Akt/FoxO signaling in a muscle cell. In another embodiment, inhibiting Trim32 protein in a muscle cell according to the present invention results in enhancing glucose uptake in a muscle cell. In another embodiment, inhibiting Trim32 protein in a muscle cell according to the present invention results in muscle fiber growth. In another embodiment, inhibiting Trim32 protein in a muscle cell according to the present invention results in induction of mitosis in a muscle cell.

In another embodiment, a muscle cell is a skeletal muscle cell. In another embodiment, a muscle cell is a cardiac muscle cell. In another embodiment, a muscle cell is a smooth muscle cell. In another embodiment, a muscle cell is a cell within an atrophying muscle. In another embodiment, a muscle cell is a cell of a subject afflicted with a wasting disease. In another embodiment, a muscle cell is a cell of a subject afflicted with a muscle denervation disease. In another embodiment, a muscle cell is a cell of a fasting subject. In another embodiment, a muscle cell is a cell of a subject afflicted with cachexia. In another embodiment, a muscle cell is a cell of a subject afflicted with cancer. In another embodiment, a muscle cell is a cell of a subject afflicted with sepsis. In another embodiment, a muscle cell is a cell of a subject afflicted with diabetes.

In another embodiment, a muscle cell is a cell of a subject suffering from loss of muscle mass. In another embodiment, a muscle cell is a cell of a subject suffering from accelerated degradation of myofibrillar and soluble proteins, and/or a catabolic state. In another embodiment, a muscle cell is a cell of a subject suffering from low levels of IGF-I. In another embodiment, a muscle cell is a cell of a subject suffering from low levels of insulin. In another embodiment, the method of the invention inhibits and/or downregulates Trim32 and thereby reduces muscle atrophy.

In another embodiment, the present invention further provides a method for inducing glucose uptake in a muscle cell, comprising the step of increasing the abundance of plakoglobin protein in the cell, thereby inducing glucose uptake in a muscle cell. In another embodiment, increasing the abundance of plakoglobin protein in the cell further results in inducing muscle fiber growth. In another embodiment, increasing the abundance of plakoglobin protein in a cell results in inducing the phosphorylation of insulin receptor in the cell. In another embodiment, increasing the abundance of plakoglobin protein in a cell is transfecting the cell with a vector comprising a nucleic acid molecule encoding the plakoglobin protein. In another embodiment, increasing the abundance is increasing the concentration. In another embodiment, increasing the abundance is increasing the activity.

In another embodiment, activation of the PI3K/Akt/FoxO pathway according to the invention induces cell growth, while its inhibition reduces cell survival and in muscle, causes atrophy. In another embodiment, Trim32 inhibition induces the accumulation of plakoglobin, which in turn binds to the insulin receptor and the PI3K subunit, p85, and promotes PI3K/Akt/FoxO signaling. In another embodiment, the invention further provides stabilizing plakoglobin for enhancing PI3K/Akt/FoxO signaling.

In another embodiment, plakoglobin comprises or consists the amino acid sequence: MEVMNLIEQPIK-VTEWQQTYTYDSGIHSGVNTCVPSVSSKGIMDED-DACGRQYTLKKTT TYTQGVPQNQGDLEYQMSTTA-RAKRVREAMCPGVSGEDSSLLLATQVEGQTTNLQRL AEPSQLLKSAIVHLINYQDDAELATRALPELTKLLND-EDPVVVTKAAMIVNQLSKKEAS RRALMG-SPQLVAAVVRTMQNTSDLDTARCTTSILHNLSHH-REGLLAIFKSGGIPALVRM LSSPVESVLFYAITTLHN-LLLYQEGAKMAVRLADGLQKMVPLLNKNNPK-FLAITTDCLQ LLAYGNQESKLIILANGGPQGLVQIMR-NYSYEKLLWTTSRVLKVLSVCPSNKPAIVEAG GMQALGKHLTSNSPRLVQNCLWTLRNLSDVAT-KQEGLESVLKILVNQLSVDDVNVLTC ATGTLSN-LTCNNSKNKTLVTQNSGVEALIHAILRAGDKD-DITEPAVCALRHLTSRHPEAE MAQNSVRLN-YGIPAIVKLLNQPNQWPLVKATIGLIRNLALCPAN-HAPLQEAAVIPRLVQ LLVKAHQDAQRHVAAGTQQP-YTDGVRMEEIVEGCTGALHILARDPMNRMEIFRLN-TIPL FVQLLYSSVENIQRVAAGVLCELAQDKEAADAI-DAEGASAPLMELLHSRNEGTATYAA AVLFRISEDKN-PDYRKRVSVELTNSLFKHDPAAWEAAQSMIPINEPY-ADDMDATYRPM YSSDVPLDPLDMHMDLDGDYPM-DTYSDGLRPPYPTADHMLA (SEQ ID NO: 3). In another embodiment, plakoglobin is a fragment of SEQ ID NO: 3 having a plakoglobin activity as described herein. In another embodiment, plakoglobin is a mutant of SEQ ID NO: 3 having a plakoglobin activity as described herein.

In another embodiment, the invention surprisingly provides that plakoglobin is an important constituent of skeletal muscle where it binds to both the insulin receptor and the p85 regulatory subunit of PI3K, to enhance signaling by the PI3K/Akt/FoxO cascade. Thus, in some embodiments, changes in plakoglobin levels alone influence PI3K/Akt/FoxO pathway in muscle and thereby causes muscle growth or block atrophy. In another embodiment, the invention surprisingly provides that Trim32 functions as a novel inhibitor of PI3K/Akt/FoxO signaling by promoting the degradation of plakoglobin, which is important for activation of this pathway in a cell.

In another embodiment, downregulation of Trim32 reduces muscle atrophy. In another embodiment, downregulation of Trim32 is achieved by electroporation of a dominant negative Trim32 (Trim32-DN), which lacks the catalytic RING domain. In another embodiment, overexpression of Trim32-DN results in increase in weight over that of muscles electroporated (FIG. 1A). In another embodiment, a nucleic acid molecule encoding a protein of the invention is delivered into a target muscle tissue by in vivo electroporation.

In some embodiments, any protein or a polypeptide described herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides even more stable while in a body or more capable of penetrating into cells. In some embodiments, the terms "protein" and "polypeptide" are used interchangeably.

In some embodiments, modifications to a protein of the invention include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, polypeptide bonds (—CO—NH—) within the polypeptide are substituted. In some embodiments, the polypeptide bonds are substituted by N-methylated bonds (—N(CH3)-CO—). In some embodiments, the polypeptide bonds are substituted by ester bonds (—C(R)H—C—O—O—C(R)—N—). In some embodiments, the polypeptide bonds are substituted by ketomethylen bonds (—CO—CH2-). In some embodiments, the polypeptide bonds are substituted by α-aza bonds (—NH—N(R)—CO—), wherein R is any alkyl, e.g., methyl, carba bonds (—CH2-NH—). In some embodiments, the polypeptide bonds are substituted by hydroxyethylene bonds (—CH(OH)—CH2-). In some embodiments, the polypeptide bonds are substituted by thioamide bonds (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and even at several (2-3 bonds) at the same time.

In some embodiments, natural aromatic amino acids of the polypeptide such as Trp, Tyr and Phe, be substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g. fatty acid, complex carbohydrates etc).

In one embodiment, "amino acid" or "amino acid" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acid.

In some embodiments, the polypeptides of the present invention are utilized in therapeutics which requires the polypeptides to be in a soluble form. In some embodiments, the polypeptides of the present invention include one or more non-natural or natural polar amino acid, including but not limited to serine and threonine which are capable of increasing polypeptide solubility due to their hydroxyl-containing side chain.

In some embodiments, the polypeptides of the present invention are utilized in a linear form, although it will be appreciated by one skilled in the art that in cases where cyclicization does not severely interfere with polypeptide characteristics, cyclic forms of the polypeptide can also be utilized.

In some embodiments, the polypeptides of present invention are biochemically synthesized such as by using standard solid phase techniques. In some embodiments, these biochemical methods include exclusive solid phase synthesis, partial solid phase synthesis, fragment condensation, or classical solution synthesis. In some embodiments, these methods are used when the polypeptide is relatively short (about 5-15 kDa) and/or when it cannot be produced by recombinant techniques (i.e., not encoded by a nucleic acid sequence) and therefore involves different chemistry.

In some embodiments, solid phase polypeptide synthesis procedures are well known to one skilled in the art and further described by John Morrow Stewart and Janis Dillaha Young, Solid Phase Polypeptide Syntheses (2nd Ed., Pierce Chemical Company, 1984). In some embodiments, synthetic polypeptides are purified by preparative high performance liquid chromatography [Creighton T. (1983) Proteins, structures and molecular principles. WH Freeman and Co. N.Y.] and the composition of which can be confirmed via amino acid sequencing by methods known to one skilled in the art.

In some embodiments, recombinant protein techniques are used to generate the polypeptides of the present invention. In some embodiments, recombinant protein techniques are used for generation of relatively long polypeptides (e.g., longer than 18-25 amino acid). In some embodiments, recombinant protein techniques are used for the generation of large amounts of the polypeptide of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al, (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In one embodiment, a polypeptide of the present invention is synthesized using a polynucleotide encoding a polypeptide of the present invention. In some embodiments, the polynucleotide encoding a polypeptide of the present invention is ligated into an expression vector, comprising a transcriptional control of a cis-regulatory sequence (e.g., promoter sequence). In some embodiments, the cis-regulatory sequence is suitable for directing constitutive expression of the polypeptide of the present invention. In some embodiments, the cis-regulatory sequence is suitable for directing tissue specific expression of the polypeptide of the present invention. In some embodiments, the cis-regulatory sequence is suitable for directing inducible expression of the polypeptide of the present invention. In some embodiments, the vector is a cationic vector.

In some embodiment, tissue-specific promoters such as muscle specific promoters suitable for use with the present invention include sequences which are functional in specific cell population, such as the neurofilament promoter [Byrne et al. (1989) Proc. Natl. Acad. Sci. USA 86:5473-5477]. Inducible promoters suitable for use with the present invention include for example the tetracycline-inducible promoter (Srour, M. A., et al., 2003. Thromb. Haemost. 90: 398-405).

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above). In another embodiment, a cDNA of the invention encodes a TRIM 32 protein. In another embodiment, a cDNA of the invention encodes a TRIM 32 protein having SEQ ID NO: 1. In another embodiment, a cDNA of the invention encodes a DN TRIM 32 protein. In another embodiment, a cDNA of the invention encodes a DN TRIM 32 protein having SEQ ID NO: 2.

In one embodiment, "complementary polynucleotide sequence" refers to a sequence, which results from reverse transcription of messenger RNA using a reverse transcriptase or any other RNA dependent DNA polymerase. In one embodiment, the sequence can be subsequently amplified in vivo or in vitro using a DNA polymerase. In another embodiment, a cDNA of the invention encodes a plakoglobin. In another embodiment, a cDNA of the invention encodes a plakoglobin having SEQ ID NO: 3.

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In one embodiment, the polynucleotides of the present invention further comprise a signal sequence encoding a signal peptide for the secretion of the polypeptides of the present invention. In some embodiments, signal sequences include, but are not limited to the endogenous signal sequence. In one embodiment, following expression and secretion, the signal peptides are cleaved from the precursor proteins resulting in the mature proteins. In one embodiment, the polynucleotides of the present invention are transferred into the target tissue/muscle. In one embodiment, the polynucleotides of the present invention are electro-transferred into the target tissue/muscle.

In some embodiments, polynucleotides of the present invention are prepared using PCR techniques, or any other method or procedure known to one skilled in the art. In some embodiments, the procedure involves the legation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhances) and transcription and translation terminators (e.g., polyadenylation signals).

In one embodiment, a variety of prokaryotic or eukaryotic cells can be used as host-expression systems to express the polypeptides of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g. mammalian expression systems such as CHO cells) to express the polypeptide of the present invention. In one embodiment, the expression vector used to express polynucleotides of the present invention in mammalian cells is pCI-DHFR vector comprising a CMV promoter and a neomycin resistance gene. Construction of the pCI-DHFR vector is described, according to one embodiment, in Example 1.

In some embodiments, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of *E. coli* expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors are useful for in vivo expression of the polypeptides of the present invention since they offer advantages such as lateral infection and targeting specificity. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, introduction of nucleic acid by viral infection offers several advantages over other methods such as lipofection and electroporation, since higher transfection efficiency can be obtained due to the infectious nature of viruses.

In one embodiment, it will be appreciated that the polypeptides of the present invention can also be expressed from a nucleic acid construct administered to the individual employing any suitable mode of administration, described hereinabove (i.e., in-vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

In one embodiment, in vivo gene therapy using EPO has been attempted in animal models such as rodents [Bohl et al., Blood. 2000; 95:2793-2798], primates [Gao et al., Blood, 2004, Volume 103, Number 9] and has proven successful in human clinical trials for patients with chronic renal failure [Lippin et al Blood 2005, 106, Number 7].

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods, in some embodiments, can be used to introduce the expression vector of the present invention into the host cell system. In some embodiments, such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, transformed cells are cultured under effective conditions, which allow for the expression of high amounts of recombinant polypeptide. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides of the present invention either remain within the recombinant cell, secreted into the fermentation medium, secreted into a space between two cellular membranes, such as the periplasmic space in *E. coli*; or retained on the outer surface of a cell or viral membrane.

In one embodiment, following a predetermined time in culture, recovery of the recombinant polypeptide is effected.

In one embodiment, the phrase "recovering the recombinant polypeptide" used herein refers to collecting the whole fermentation medium containing the polypeptide and need not imply additional steps of separation or purification.

In one embodiment, polypeptides of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide of the present invention is retrieved in "substantially pure" form.

In one embodiment, the phrase "substantially pure" refers to a purity that allows for the effective use of the protein in the applications described herein.

In one embodiment, the polypeptide of the present invention can also be synthesized using in vitro expression systems. In one embodiment, in vitro synthesis methods are well known in the art and the components of the system are commercially available.

In one embodiment, a protein of the present invention can be provided to an individual/subject per se. In one embodiment, the protein of the present invention can be provided to the individual as part of a pharmaceutical composition where it is mixed with a pharmaceutically acceptable carrier. In another embodiment, the protein of the present invention can be provided to the individual as part of a pharmaceutical composition where it is mixed with at least one additional anti-inflammatory agent and a pharmaceutically acceptable carrier.

In one embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In one embodiment, "active ingredient" refers to the protein of interest, which is accountable for the biological effect.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In one embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In one embodiment, the preparation is administered in a local rather than systemic manner, for example, via injection of the preparation directly into a specific region of a patient's body.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.012% to about 0.933% of the desired compound or compounds, or in another embodiment, from about 0.033% to about 0.7%.

In some embodiments, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In some embodiments, h compositions comprise from about 0.01% to about 10.0% w/v of a subject compound, more preferably from about 0.1% to about 2.0, which is used for systemic delivery of the compounds by the intranasal route.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of the active ingredients to allow for the preparation of highly concentrated solutions.

In another embodiment, the active compound can be delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. *Biomed. Eng.* 14:201 (1987); Buchwald et al., Surgery 88:507 (1980); Saudek et al., *N. Engl. J. Med.* 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in *Medical Applications of Controlled Release*, supra, vol. 2, pp. 115-138 (1984). Other controlled release systems are discussed in the review by Langer (*Science* 249:1527-1533 (1990).

In some embodiments, the active ingredient is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In some embodiments, pharmaceutical compositions suitable for use in context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

The compositions also comprise preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise local anesthetics or other actives. The compositions can be used as sprays, mists, drops, and the like.

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also be prepared, placed in an appropriate container, and labeled for treatment of an indicated condition.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the proteins of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

In Vivo Transfection

Animal experiments were conducted according to the ethical guidelines of the NIH Guide for the Care and Use of Laboratory Animals. Animal care was provided by specialized personnel in the Institutional Animal Care facility. Experiments were performed in adult CD-1 male mice (27-28 g). In vivo electroporation was performed by the injection of 20 µg of plasmid DNA into adult mouse tibialis anterior muscle and application in of electric pulses (12V, 5 pulses, 200-ms intervals). In fasting experiments food was removed from cages 4 days after electroporation for 48 hours. Fiber size was determined by measurements of cross-sectional area of 500 transfected (express GFP) and 500 adjacent nontransfected fibers in the same muscle section (10 m), using MetaMorph (Molecular Devices).

Antibodies and Constructs.

The Trim32 and control shRNAs were previously described (shTrim32-1, GGCTGATTGGTGTCACTGATA (SEQ ID NO: 5); shTrim32-2, AGCTGCTGGTCTTG-GACTGTT (SEQ ID NO: 6); shLacz, AAATCGCTGATTT-GTGTAGTC (SEQ ID NO: 7), and the plakoglobin shRNA was designed using Invitrogen's BLOCK-iT RNAi expression vector kit with the pcDNA 6.2-GW/EmGFP-miR vector. Anti plakoglobin, Laminin and GAPDH are from Sigma. Anti-tubulin from Invitrogen and anti GFP from abcam. Anti Akt, P-Akt, PI3K-p85, P-PI3K-p85, FOXO3 and P-FOXO3 are from Cell Signaling.

Protein Analysis

Immunoblotting and immunoprecipitation were performed as follows: the cytosolic fraction from tibialis anterior muscle was used for immunoblotting or immunoprecipitation and was resolved by SDS-PAGE and immunoblotting with specific antibodies and secondary antibodies conjugated to alkaline phosphatase. Immunoprecipitation assays of plakoglobin or PI3K-p85 from the soluble fraction of muscle were performed overnight at 4° C. and then protein A/G agaroze was added for 4 hours. Phosphatase inhibitors were not added to extraction buffer except for the immunoprecipitation experiments and blots in FIG. 5A (1 mM Na3VO4 and 50 mM NaF).

Quantitative Real-Time PCR

Total RNA was isolated from muscle and cDNA synthesized by reverse transcription. Real-time qPCR was performed on mouse target genes using specific primers (Table 1) and DyNAmo HS SYBR Green qPCR kit (F-410S; Finnzymes) according to the manufacturers' protocol.

TABLE 1 qPCR primers and shRNA oligos used in the present study

| Sequence (5' to 3') | Gene | DNA |
|---|---|---|
| GGCTGATTGGTGTCACTGATA (SEQ ID NO: 8) | Trim32 | shRNA 1 |
| AGCTGCTGGTCTTGGACTGTT (SEQ ID NO: 9) | Trim32 | shRNA 2 |
| GGAACTACAGCTACGAGAAGC (SEQ ID NO: 10) | Plakoglobin | shRNA |
| GGGCATCATGGATGAGGATGA (SEQ ID NO: 11) | Plakoglobin | shRNA |
| AGACCGGAAACATCATCTCTT (SEQ ID NO: 12) | Desmoplakin | shRNA |
| CAAAGAGAAATGGCTTCCCTA (SEQ ID NO: 13) | Desmoplakin | shRNA |
| TGGGTGTATCGGATGGAGAC (SEQ ID NO: 14) | Atrogin1 | qPCR primer Forward |
| TCAGCCTCTGCATGATGTTC (SEQ ID NO: 15) | Atrogin1 | qPCR primer Reverse |
| GTCCATGTCTGGAGGTCGTT (SEQ ID NO: 16) | MuRF1 | qPCR primer Forward |
| AGGAGCAAGTAGGCACCTCA (SEQ ID NO: 17) | MuRF1 | qPCR primer Reverse |
| ACCCAGAAGACTGTGGATGG (SEQ ID NO: 18) | GAPDH | qPCR primer Forward |
| CACATTGGGGGTAGGAACAC (SEQ ID NO: 19) | GAPDH | qPCR primer Reverse |
| CTGTGTGCCCTCTGTAAGCA (SEQ ID NO: 20) | Plakoglobin | qPCR primer Forward |
| GAACTGTCCTCGCCTGAGAC (SEQ ID NO: 21) | Plakoglobin | qPCR primer Reverse |

Immunofluorescence

Figures 2A, 2B:
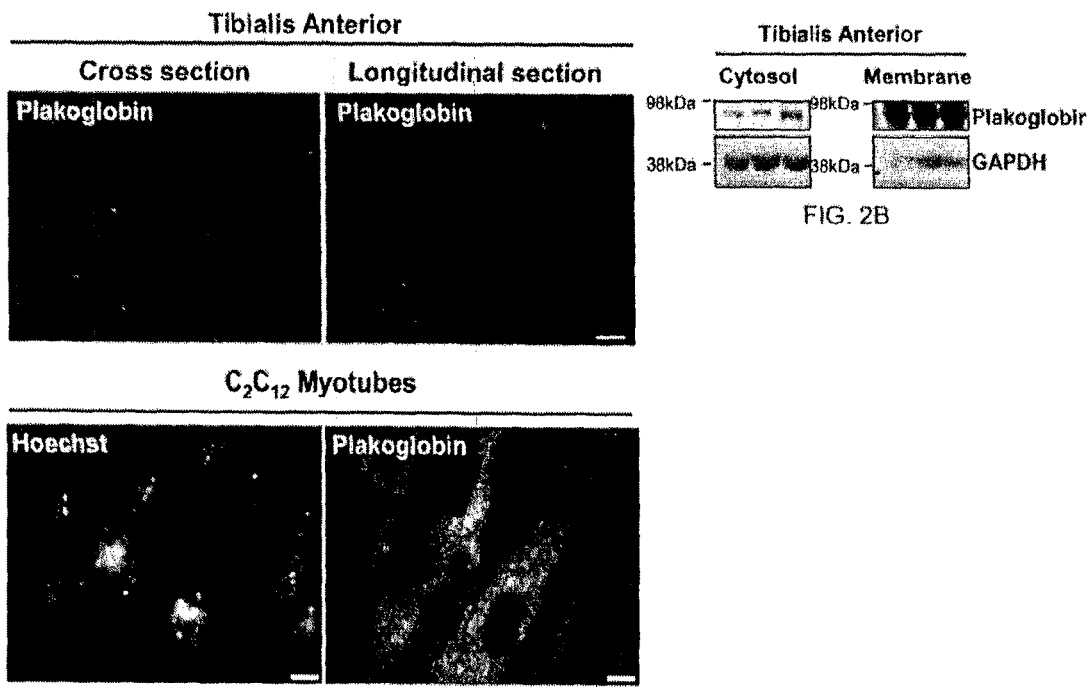
FIG. 2. Plakoglobin is present in skeletal muscle. (A) micrographs showing paraffin-embedded longitudinal and cross sections of TA muscles from fed mice (Scale bar=20 μm) (top), and C2C12 myotubes (Scale bar=15 μm) (bottom) were stained with anti plakoglobin. (B) a gel micrograph showing that plakoglobin is present in the cytosolic and membrane fractions of muscle. 0.25% of membrane fraction and 0.01% of cytosolic fraction were analyzed by immunoblotting. GAPDH serves as a cytosolic marker.

Immunofluorescence of paraffin-embedded muscle sections was performed as follows: muscle cross or longitudinal sections from fed and fasted mice were embedded in paraffin and then gradually rehydrated in ethanol/PBS. For immunofluorescence of rehydrated samples 1:50 dilution of primary antibody and 1:1000 dilution of Alexa 555 conjugated secondary antibody were used. In FIG. 2A, C2C12 cells were plated on a glass-bottom 12-well plate (P12G-1.5-14-F, MatTek Corporation), which was coated with 5 ug/ml fibronectin (f1141, Sigma). Cells were differentiated into myotubes and then fixed in 4% PFA for 15 min at room temperature. Following 15 min of blocking in 50 mg/ml BSA/TBS-T, immunofluorescence analysis was performed using 1:50 dilution of plakoglobin antibody and 1:1000 dilution of Alexa 555 conjugated secondary antibody, all diluted in blocking solution. Images were collected at room temperature using a Nikon Ti-E inverted motorized microscope with a Plan Apo 1.4 NA objective lens, a 545/30 excitation filter and 620/60 emission filter (Alexa 555), a 620/60 excitation filter and 700/75 emission filter (Alexa 647), a Hamamatsu ORCA-R2 cooled CCD camera and MetaMorph 7 software.

Glucose Uptake Assay

C2C12 cells were plated on a 6-well plate coated with 5 ug/ml fibronectin (f1141, Sigma). Forty two hours after transfection (lipofectoamine 2000), cells were washed in warm PBS, starved in DMEM/0.1% BSA for 6 hours and washed again. Following treatment with 200 nM insulin/PBS (Sigma, I0516) for 30 min at 37° C., cells were washed and incubated for 10 min at 37° C. with 1 uCi/ml 2-deoxy-D-[3H]glucose (NET328A250UC, PerkinElmer) and 0.1 mM cold 2-deoxy-D-glucose (D8375, Sigma). 20 nM of cytochalasin B (glucose transport inhibitor) (C6762, Sigma) were added to control wells. Then, cells were washed in cold PBS, lyzed in 0.2N NaOH for 2 hours at room temperature, and radioactivity determined using scintillation fluid.

Fractionation of Muscle Tissue.

Work was performed at 4° C. Mouse tibialis anterior muscles were homogenized on ice for 30 s in 19 volumes of buffer C (20 mM Tris-HCl, pH 7.6, 5 mM EDTA/NaOH pH 7.4, 100 mM KCl, 1 mM DTT and 1 mM sodium Ortho-Vanadate), and spun at 2900×g for 20 min to pellet nuclei and unbroken tissue.

The supernatant was centrifuged at 180,000×g for 90 min and the supernatant (i.e., cytosolic fraction) stored at −80° C. The pellet was resuspended in 10 volumes of buffer M (20 mM Tris-HCl, pH 7.6, 5 mM EDTA/NaOH pH 7.4, 100 mM KCl, 1 mM DTT, 0.25% sodium deoxycholate, 1% NP-40 and 1 mM sodium OrthoVanadate), rotated at 4° C. for 20 min and centrifuged at 100,000×g for 30 min. The supernatant (i.e., membrane fraction) was then collected and stored at −80° C. All buffers contained protease inhibitors (10 g/ml leupeptin, 3 mM benzamidine, 1 g/ml trypsin inhibitor, and 1 mM PMSF). 0.25% of membrane fraction and 0.01% of cytosolic fraction were separated on SDS-PAGE for Western Blot analysis.

Statistical Analysis and Image Acquisition

Data are presented as means±SEM. The statistical significance was determined with one-tailed paired Student's t test. Alpha level was set to 0.05. Muscle sections were imaged at room temperature with an upright fluorescent microscope (Nikon 80i) and a monochrome camera (Hamamatsu C8484-03), and C2C12 myotubes with Nikon Ti-E inverted motorized microscope and a Hamamatsu ORCA-R2 cooled CCD camera. Image acquisition and processing was performed using MetaMorph software. Black and white images were processed with Adobe Photoshop CS3, version 10.0.1. software.

In Vitro Ubiquitination

A plasmid DNA encoding His-plakoglobin was electroporated into tibialis anterior muscle and 4 d later the food was removed from cages for 2 days. His-plakoglobin was purified from muscle homogenates using Ni-Column and subjected to ubiquitination reaction containing 22.5 nM E1, 0.75 M E2, 0.4 M Trim32, 0.75 M UbcH5 and 59 M ubiquitin in reaction buffer (2 mM ATP, 20 mM Tris-HCl, pH 7.6, 20 mM KCl, 5 mM MgCl2, and 1 mM DTT). Plakoglobin ubiquitination was analyzed by SDS-PAGE and immunoblotting with plakoglobin antibody (Sigma).

Immunofluorescence

A vector encoding GFP-plakoglobin was electroporated into tibialis anterior of adult wild-type mouse for 6 d. Muscle cross sections were paraffin-embedded as reported and images were collected at room temperature using an upright epifluorescence microscope (model 80i; Nikon) with a Plan Fluor 40×1.4 NA objective lens, a 545/30 excitation filter and 620/60 emission filter (Chroma Technology Corp.) and a cooled CCD camera (model C8484-03; Hamamatsu Photonics).

DNA Constructs

The desmoplakin shRNA was designed using Invitrogen's RNAi esigner tool, and cloned into pcDNA 6.2-GW/EmGFP-miR vector using Invitrogen's BLOCK-iT RNAi expression vector kit.

Example 1: Trim32 Inhibition Induces Normal Muscle Growth

Figure 1B:
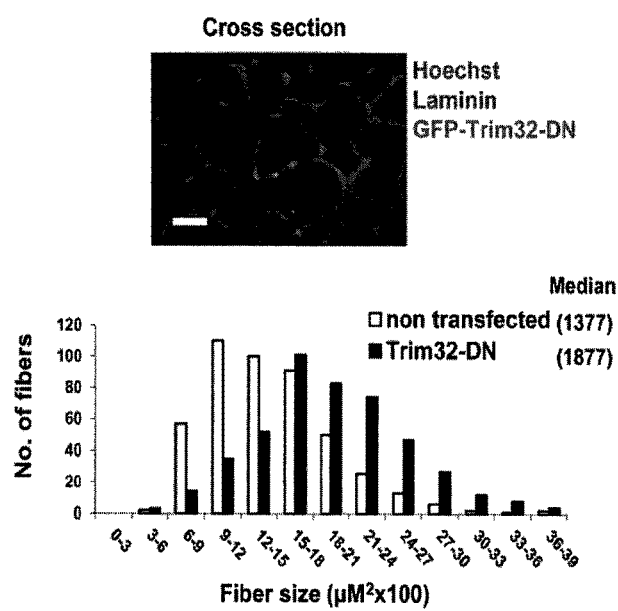

Because downregulation of Trim32 reduces muscle atrophy, the experiment also determined whether it also affects normal muscle mass by electroporation of a dominant negative Trim32 (Trim32-DN), which lacks the catalytic RING domain (Kano et al., 2008), into normal tibialis anterior muscle (TA). Overexpression of Trim32-DN for 6 days resulted in a 15% increase in weight over that of muscles electroporated with a control vector (FIG. 1A). Since not all fibers were transfected, the growth induced by Trim32 inhibition must be even greater. In fact, the mean cross-sectional area of 500 fibers expressing Trim32-DN was much larger than that of 500 non-transfected ones (FIG. 1B). Thus, Trim32 must function normally to limit muscle growth and suppression of this ubiquitin ligase alone can induce muscle hypertrophy.

Example 2: Plakoglobin is Present in Skeletal Muscle

Figure 7A:
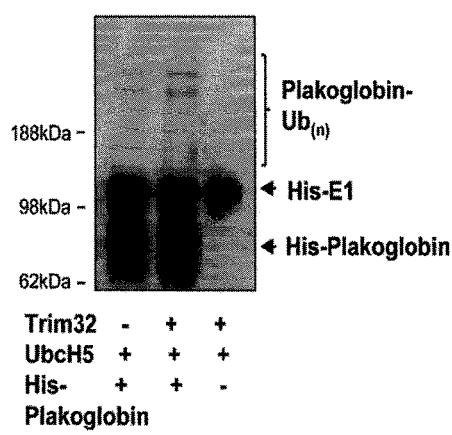
FIG. 7. Recombinant Trim32 polyubiquitinates 6His-Plakoglobin. (A) Is a micrograph showing 6His-plakoglobin that was expressed and purified from normal muscle and then incubated with Trim32, UbcH5, ubiquitination and ATP for 90 minutes. The 6His-tagged ubiquitinated plakoglobin was isolated with a Ni column, and analyzed by SDS-PAGE and immunoblot using anti plakoglobin. (B) is a bar graph showing that plakoglobin expression does not decrease during fasting. Quantitative RT-PCR of mRNA preparations from atrophying and control muscles expressing shLacz or Trim32-DN, using primers for MuRF1 and Atrogin1. Data is plotted as the mean fold change relative to fed control. n=4. * p<0.005 vs. shLacz in fed.
Figure 7B:
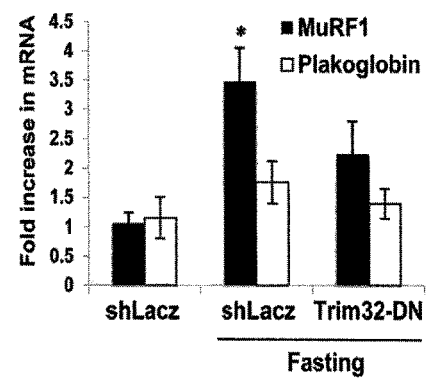

The present findings suggest that Trim32 substrates accumulate upon its downregulation and reduce atrophy or induce growth. Using immobilized GST-Trim32 and Mass Spectrometry, several Trim32 substrates were identified in muscle extracts, which were bound and could be ubiquitinated by Trim32, including thin filament and Z-band components, plus the cytoskeletal protein desmin. Surprisingly, the immobilized Trim32 also bound plakoglobin, which, in other tissues, is a component of the desmosome complex. Its presence was unexpected because there had been no prior reports of desmosomes or its components in skeletal muscle. To determine whether it is ubiquitinated by Trim32, GST-Trim32 precipitates were incubated with a ubiquitination system containing E1, E2 (UbcH5), ATP, and 6His-ubiquitin. The 6His-tagged ubiquitinated proteins were then purified with a nickel column. Mass spectrometric analysis revealed that plakoglobin was polyubiquitinated by Trim32 (as documented by the presence of 13 unique peptides). Furthermore, recombinant Trim32 also polyubiquitinated 6His-plakoglobin, which was expressed and purified from normal muscle (FIG. 7).

In epithelial cells, binding of PI3K to plakoglobin was proposed to enhance PI3K/Akt signaling (Calautti et al., 2005; Woodfield et al., 2001). Because this pathway is the primary regulator of muscle mass. However, it was important initially to confirm that plakoglobin is actually present in the satellite cells and muscle fibers. Therefore, its spatial distribution in normal tibialis anterior (TA) was analyzed by immunofluorescence staining of paraffin-embedded cross and longitudinal sections. In epithelia, plakoglobin has a punctate distribution throughout the cell (Chen et al., 2002; Nathke et al., 1994). A similar spot-like distribution of plakoglobin was found within the muscle fiber, and in the plane of the fiber membrane (FIG. 2A). Thus, this protein, unlike myofibrillar components or desmin, did not show a specific periodic distribution along the sarcomere. A similar diffuse distribution of plakoglobin was observed in C2C12 myotubes (FIG. 2A). Furthermore, the presence of this protein in the soluble phase and on the muscle membrane was confirmed biochemically by fractionation of TA muscle (FIG. 2B).

Example 3: Trim32 Knockdown in Fasting Increases PI3K/Akt Activity

Figures 3A, 3B, 3C, 3D:
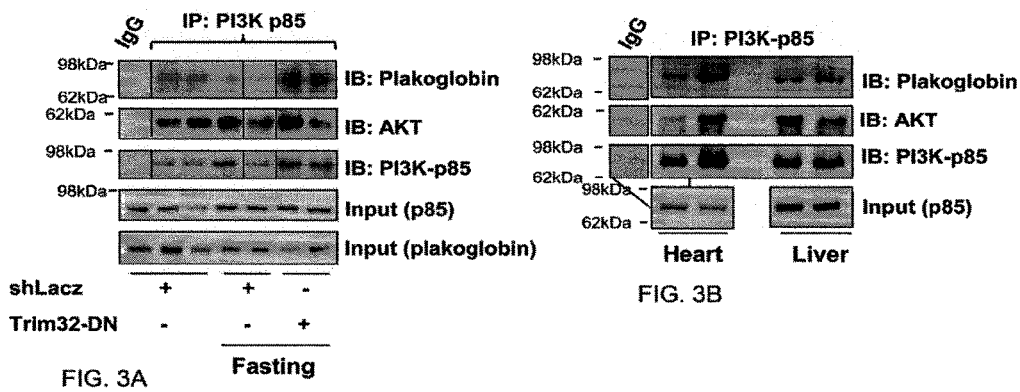
FIG. 3. Trim32 downregulation during fasting inhibits the decrease in PI3K/Akt/FoxO signaling. (A) is a gel micrograph showing that during fasting, inhibition of Trim32 enhances the interaction of plakoglobin with p85/PI3K. p85/PI3K was immunoprecipitated from the soluble fraction of muscles expressing shLacz or Trim32-DN from fed or fasted mice. Precipitates were analyzed by immunoblotting. (B) is a gel micrograph showing that plakoglobin and p85/PI3K interact in heart and liver. p85/PI3K was immunoprecipitated from the soluble fraction of heart and liver from fed mice and analyzed by immunoblotting. (C) is a gel micrograph showing that during fasting, downregulation of Trim32 increases PI3K/Akt/FoxO signaling. Soluble fractions of normal and atrophying muscles expressing shLacz or shTrim32 were analyzed by SDS-PAGE and immunoblot. (D) are bar graphs showing that inhibition of Trim32 reduces MuRF1 and Atrogin1 expression during fasting. Quantitative RT-PCR of mRNA preparations from atrophying and control muscles expressing shLacz or Trim32-DN using primers for MuRF1 and Atrogin1. Data is plotted as the mean fold change relative to fed control. n=4. * p<0.05 vs. shLacz in fed # p<0.05 vs. shLacz in fasting.

To determine whether plakoglobin loss influences the activity of the PI3K/Akt/FoxO pathway, as had been suggested in keratinocytes (Calautti et al., 2005), the question of whether plakoglobin interacts with p85/PI3K in muscle was tested. Plakoglobin co-precipitated with p85/PI3K from normal muscle, but not during fasting (FIG. 3A), where PI3K/Akt/FoxO signaling (FIG. 3C) was reduced. This effect seemed to require Trim32 since inhibition of Trim32 during fasting by electroporation of Trim32-DN resulted in a greater association of plakoglobin with p85/PI3K (FIG. 3A). Thus, during fasting, Trim32 reduces the interaction of plakoglobin and p85/PI3K in muscle. In addition, it was determined whether these interactions were unique to muscle or whether plakoglobin might regulate this signaling pathway Similar interactions between p85/PI3K and plakoglobin were demonstrated by co-immunoprecipitation in the heart and liver (FIG. 3B) and thus, are probably functioning in most, perhaps all, cells.

Further studies determined whether the interaction of plakoglobin with p85/PI3K, in fact, influences PI3K/Akt/FoxO signaling. By two days after food deprivation, phosphorylation of PI3K, Akt, and its target FoxO3 was markedly reduced (FIG. 3C) (Sandri et al., 2004; Stitt et al., 2004). However, downregulation of Trim32 almost completely blocked this response to fasting. In fact, levels of phosphorylated PI3K, Akt, and FoxO3 were similar to those in muscles from fed mice (FIG. 3C). Normally during fasting, FoxO is activated (dephosphorylated) and stimulates the expression of a set of atrophy-related genes, including the ubiquitin ligases MuRF1 and Atrogin1, which are essential for rapid fiber atrophy (Bodine et al., 2001; Gomes et al., 2001) (FIG. 3D).

However, Trim32 inhibition by overexpression of the Trim32-DN resulted in a marked decrease in MuRF1 and Atrogin1 expression in the TA muscles during fasting (FIG. 3D). This inhibition of atrogene expression during fasting together with the maintenance of normal PI3K/Akt/mTOR signaling can account for the dramatic blockage of muscle wasting observed previously. Thus, during fasting, Trim32 function must be critical in causing the reduction in PI3K/Akt/FoxO signaling that triggers the decrease in protein synthesis, the FoxO-mediated expression of the atrogene program, and muscle wasting.

To learn whether this reduction in PI3K/Akt/FoxO signaling upon fasting is dependent on the presence of plakoglobin, plakoglobin was downregulated by transfection of shRNA (shJUP) into normal muscle (FIG. 4A). The resulting fall in plakoglobin led to decreased phosphorylation of PI3K, Akt, and FOXO3. Thus, plakoglobin is required for normal signaling through the PI3K/Akt/FoxO pathway. Accordingly, when plakoglobin was downregulated with shRNA in normal muscle for 6 days, atrophy of the muscle fibers became evident (FIG. 4B). The mean cross-sectional area of 500 fibers expressing shJUP was smaller than that of 500 non-transfected fibers (FIG. 4B).

Although expressing the Trim32-DN prevented the decrease in PI3K/Akt/FoxO signaling in the atrophying muscles, this effect was markedly attenuated by simultaneously downregulating plakoglobin (FIG. 4C). Thus, plakoglobin appears critical for the Trim32-induced reduction in phosphorylation of PI3K, Akt, and FOXO3 (FIG. 4C).

Figure 8:
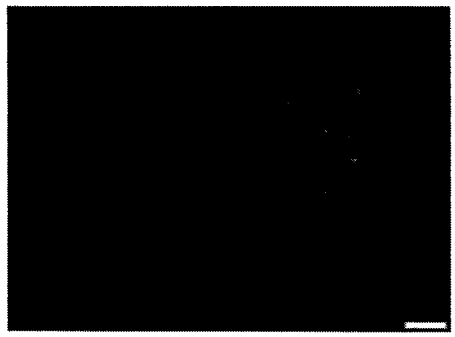
FIG. 8. Distribution of GFP-plakoglobin in muscle. A micrograph showing that GFP-Plakoglobin expressed in TA muscle shows a similar distribution to the endogenous protein.

In addition to regulating cell size and protein balance, the PI3K/Akt/FoxO pathway also mediates insulin's stimulation of glucose-uptake into muscle and adipose tissue. As predicted, plakoglobin downregulation in myoblasts reduced the stimulation by insulin of glucose uptake (FIG. 4D). Although plakoglobin is clearly important, overexpression of plakoglobin in normal myoblasts did not further stimulate this process (FIG. 4D). To test if plakoglobin mediates insulin-dependent glucose uptake and activates PI3K/Akt/FoxO signaling by interacting with the insulin receptor, plakoglobin was immunoprecipitated from normal and atrophying muscles (FIG. 4E). The insulin receptor co-precipitated together with plakoglobin from normal muscle. During fasting, when Trim32 is active plakoglobin remained associated with the insulin receptor (FIG. 4E). Plakoglobin thus binds to the insulin receptor and seems to serve as a key component in its interactions with and activation of PI3K. Similar interactions between plakoglobin and the insulin receptor were also observed in heart and liver (FIG. 4F), suggesting that, in many tissues, plakoglobin functions to regulate insulin-dependent activation of PI3K. Together, these observations predict that increasing the level of plakoglobin during fasting should lead to greater activity of the insulin receptor and PI3K/Akt/FoxO pathway. Accordingly, during fasting, overexpression of GFP-tagged plakoglobin (which showed a similar distribution to that of the endogenous protein (FIG. 8) alone enhanced phosphorylation of insulin receptor (at Y1361) and activation of PI3K/Akt/FoxO signaling (FIG. 4G). Thus, the Trim32-dependent regulation of plakoglobin function during fasting is a key new step in the reduction in PI3K/Akt/FoxO signaling in low-insulin states.

Example 4: Trim32 Inhibition Enhances PI3K/Akt/FoxO Signaling in Normal Muscle

Figure 9A:
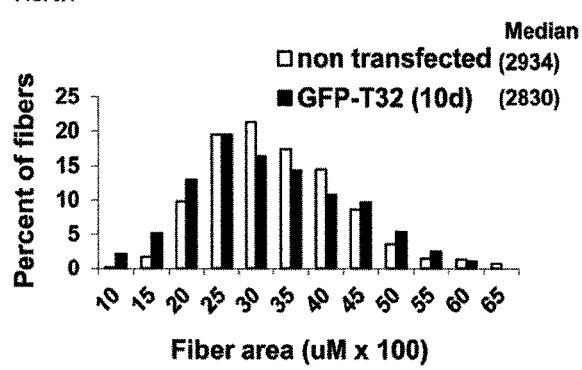
FIG. 9. Overexpression of Trim32 in normal muscle for 10 d does not induce atrophy. (A) A bar graph showing the results of cross sectional area of 500 fibers transfected with GFP-Trim32 (black) vs. 500 non transfected fibers (open) in the same muscle. n=6. (B) A gel micrograph showing normal muscles were transfected with shLacz or HA-Trim32, and soluble extracts were analyzed by SDS-PAGE and immunoblot.
Figure 9B:
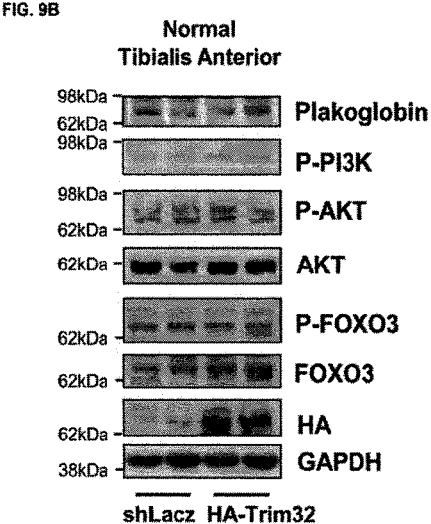

In light of these effects in fasting, it was determined whether Trim32 may also influence normal muscle mass (FIG. 1) by regulating PI3K/Akt/FoxO/mTOR activity. After electroporation of the Trim32-DN into normal TA for 6 days plakoglobin accumulated and phosphorylation of PI3K, Akt, and FOXO increased as well as of the downstream target of mTOR kinase activity, S6K (FIG. 5A). Furthermore, transfection of Trim32-DN into C2C12 myoblasts enhanced insulin-dependent glucose uptake above the levels in cells expressing a control plasmid (FIG. 5B). Thus, the growth-promoting effects of Trim32-DN are probably due to enhanced PI3K/Akt/FoxO signaling and activation of mTOR. It is noteworthy that Trim32 overexpression in normal muscle does not by itself alter plakoglobin levels, PI3K/Akt/FoxO signaling, glucose uptake, or fiber size (FIGS. 5B and 9). Therefore, an additional signal beyond Trim32 expression is probably required to promote plakoglobin ubiquitination and degradation, perhaps phosphorylation of plakoglobin (Calautti et al., 2005; Woodfield et al., 2001), as was recently found for the ubiquitination and degradation of desmin by Trim32.

Figure 6:
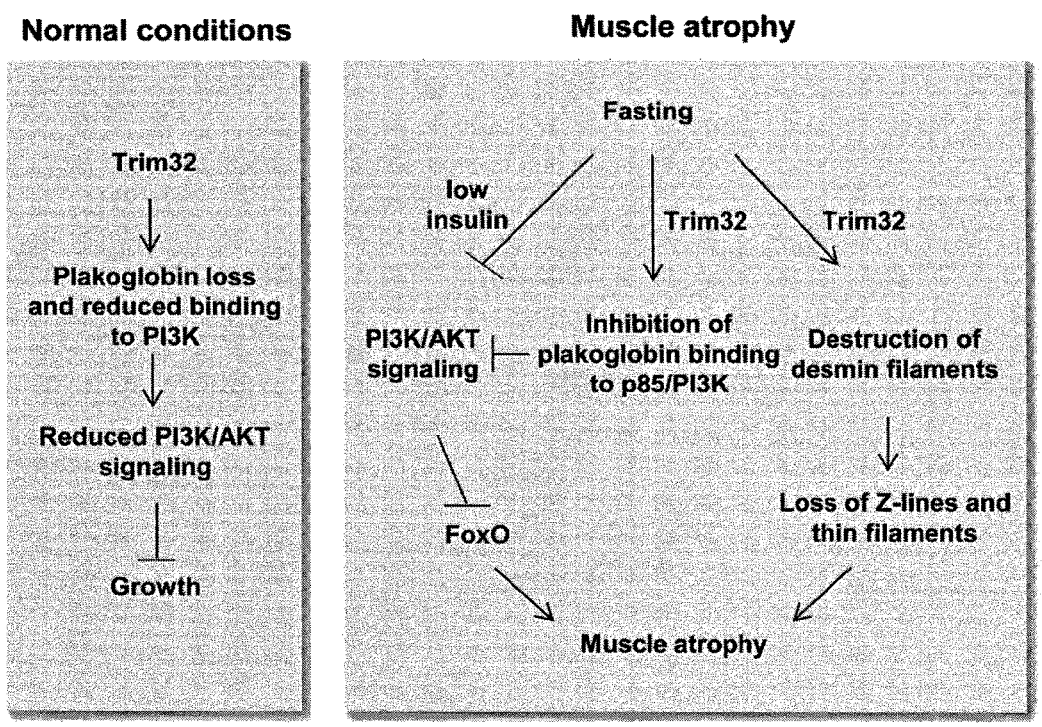
FIG. 6. Is a scheme of proposed new mechanism for regulation of PI3K/Akt/FoxO pathway by Trim32. Trim32 reduces PI3K/Akt/FoxO signaling in normal and atrophying muscle and regulates growth. In addition to its role in myofibril breakdown during fasting, Trim32 also functions as a novel inhibitor of PI3K/Akt/FoxO signaling by promoting the rapid dissociation of plakoglobin from p85/PI3K. Because Trim32 and plakoglobin are expressed in most tissues, they probably serve similar roles in regulating the growth of other cells. This novel mechanism probably contributes to the insulin resistance during fasting and catabolic diseases (e.g., diabetes, sepsis), and perhaps to the myopathies and cardiomyopathies seen with Trim32 and plakoglobin mutations.

These studies have uncovered a novel mechanism regulating the PI3K/Akt/FoxO/mTOR pathway that involves the desmosomal component plakoglobin and the ubiquitin ligase, Trim32 (FIG. 6). Because decreasing plakoglobin content reduces glucose uptake, while increasing plakoglobin levels stimulates this process (FIGS. 4C, 5A and 4G), Trim32-mediated loss of plakoglobin-p85/PI3K binding may also contribute to insulin resistance in various catabolic states (e.g. diabetes, metabolic syndrome, or sepsis). Consequently, Trim32 may represent a new therapeutic target to block muscle wasting and the insulin resistance as occurs in disease states (e.g. cancer cachexia, sepsis, and renal failure).

In normal muscle, plakoglobin downregulation reduces PI3K/Akt/FoxO signaling and causes atrophy (FIGS. 4A and B), while inhibiting Trim32 stabilizes plakoglobin, increases PI3K/Akt/FoxO activity, and induces fiber hypertrophy (FIGS. 1 and 5). Thus, in addition to being critical in atrophy, Trim32 activity also must limit the growth of normal muscle (FIG. 6). Moreover, Trim32 and plakoglobin probably serve similar roles in regulating the growth of other cells because both are expressed in most, if not all, tissues (Cowin et al., 1986; Frosk et al., 2002). In fact, plakoglobin has been shown to be an important regulator of epithelial growth (Venkiteswaran et al., 2002), and, as shown here, it binds p85/PI3K in heart and liver (FIGS. 3B and 4F), as it does in skeletal muscle (FIG. 3A). Interestingly, the close homolog of plakoglobin, beta-catenin, can also bind PI3K and enhance PI3K/Akt/FoxO signaling (Woodfield et al., 2001), and a recent study reported that beta-catenin is lost during atrophy induced by dexamethasone and accumulates during hypertrophy (Schakman et al., 2008). Plakoglobin and beta-catenin can function together in regulating gene transcription (Winn et al., 2002; Zhurinsky et al., 2000a; Zhurinsky et al., 2000b), and possibly beta-catenin may also be regulated by Trim32.

However, it is noteworthy that Trim32 overexpression alone is not sufficient to reduce plakoglobin levels or to cause atrophy (FIG. 9). Thus, the increase in PI3K/Akt/FoxO signaling with Trim32 downregulation must involve an additional signal, such as plakoglobin phosphorylation, which has been reported (Calautti et al., 2005; Woodfield et al., 2001). Accordingly, it was shown that ubiquitination of desmin by Trim32 during fasting also requires desmin phosphorylation. In normal muscle and during fasting (FIG. 4E), if Trim32 is inhibited, phosphorylation of plakoglobin may be essential for its association with insulin receptor and perhaps for it to serve as a docking site for PI3K. In any case, stabilization of plakoglobin alone increases phosphorylation of the insulin receptor and activity of the PI3K/Akt/FoxO pathway (FIG. 4G).

Figure 10A:
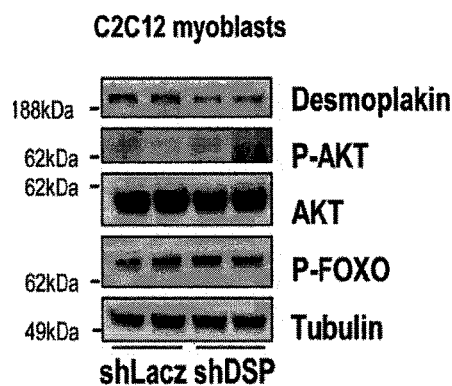
FIG. 10. Desmoplakin interacts with plakoglobin but is not essential for PI3K/Akt/FoxO signaling. (A) A gel micrograph showing that desmoplakin knockdown does not affect PI3K/Akt/FoxO signaling. C2C12 myoblasts were transfected with shLacz or shRNA to desmoplakin (shDSP), and soluble extracts were analyzed by SDS-PAGE and immunoblot. (B) A gel micrograph showing that during fasting, the association of plakoglobin and desmoplakin decreases but not when Trim32 is inhibited. Plakoglobin was immunoprecipitated from the soluble fraction of muscles expressing shLacz or Trim32-DN from fed or fasted mice. Precipitates were analyzed by immunoblotting for plakoglobin or desmoplakin.
Figure 10B:
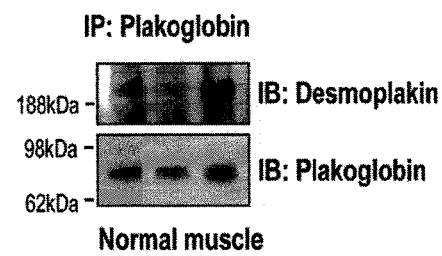

This study also provides the first evidence for the presence of the desmosomal component plakoglobin in skeletal muscle. In related studies, it was found that other components of this complex, such as desmoplakin, are present within the muscle fiber, although desmoplakin levels, unlike plakoglobin's, did not alter PI3K/Akt/FoxO signaling (FIG. 10A). In the heart, plakoglobin is part of the adhesion complexes (i.e. "desmosomes"), which are localized in the intercalated discs that link adjacent cardiomyocytes. Mice lacking plakoglobin tend to die early from cardiac rupture (Ruiz et al., 1996), and in humans, mutations in plakoglobin (Norgett et al., 2000) or the six other genes encoding desmosomal proteins (Herren et al., 2009) result in cardiac arrhythmia (Norgett et al., 2000), reduced contractility, and cardiac failure (i.e. the syndrome of "Arrhythmogenic right ventricular cardiomyopathy/dysplasia"). Perhaps, these pathological sequelae are due in part to altered signaling through the PI3K/Akt/FoxO pathway. By targeting plakoglobin or perhaps other desmosomal components for degradation in the heart, Trim32 is also likely to have important physiological or pathological effects. However, in skeletal muscle, plakoglobin does not seem to form the "classic"

desmosomes, although this protein is clearly present on the surface membrane (FIG. 2) and can be immunoprecipitated together with insulin receptor, PI3K and Akt (FIGS. 3A and 4E), as well as other components of desmosomes (FIG. 10B).

In addition to causing Limb-Girdle Muscular Dystrophy, Trim32 mutations can lead to Bardet-Biedl syndrome, which is characterized by cardiac hypertrophy and dilated cardiomyopathy (Elbedour et al., 1994). The present findings would predict that a deficiency of Trim32 could lead to excessive tissue growth and possibly inappropriate activation of PI3K/Akt/FoxO signaling. Surprisingly, Kudryashova et al. recently described a Trim32 null mouse that exhibited mild myopathies, neurogenic defects, cellular disorganization, and reduced muscle growth (Kudryashova et al., 2012; Kudryashova et al., 2011), and upon fasting or disuse (Kudryashova et al., 2012), muscles from these mice atrophy as in WT mice. These surprising observations differ markedly from the present findings on the effects of selective downregulation of Trim32 in adult muscle. Presumably, the complete deficiency of Trim32 during development causes multiple systemic defects and elicits compensatory responses, but the ability of these Trim32-deficient muscles to undergo atrophy suggest that additional ubiquitin ligases may replace Trim32 in many reactions. Conversely, expression of Trim32 rises in multiple diseases, including brains of Alzheimer patients (Yokota et al., 2006), psoriasis lesions (Liu et al., 2010) and various cancers, where it enhances invasion and metastasis (Horn et al., 2004; Kano et al., 2008). These effects may also involve Trim32-mediated degradation of plakoglobin since the loss of this protein reduces cell adhesion and increases cell migration and invasion (Gosavi et al., 2011; Kundu et al., 2008; Yin et al., 2005).

Together, these observations indicate close coupling between changes in cytoskeletal and myofibrillar components during atrophy and the cell's major growth regulatory system, which could be important in other pathological states (FIG. 6). During atrophy, Trim32 catalyzes the ubiquitination and disassembly of the desmin cytoskeleton, which is coupled to the destruction of proteins comprising the thin filament and Z-band. If desmin filaments in skeletal muscle are also linked to plakoglobin (and other desmosomal proteins), as they are in the heart (Smith and Fuchs, 1998), then the loss of plakoglobin-p85/PI3K interaction and the subsequent reduction in PI3K/Akt/FoxO signaling, may be an early event leading to the disruption of the cytoskeleton and thereby to disassembly of thin filaments.

What is claimed is:

1. A method for inducing glucose uptake in a muscle cell in a subject suffering from insulin resistance, comprising the step of inhibiting Trim32 protein in said cell in the subject suffering from insulin resistance, thereby inducing glucose uptake in a muscle cell in the subject suffering from insulin resistance.

2. The method of claim 1, wherein said muscle cell is a skeletal muscle cell.

3. The method of claim 1, wherein said inhibiting Trim32 in said cell is further inducing muscle fiber growth.

4. The method of claim 1, wherein said inhibiting Trim32 in said cell is inducing the phosphorylation of insulin receptor in said cell.

5. The method of claim 1, wherein said inhibiting Trim32 is inducing the accumulation of plakoglobin.

6. The method of claim 1, wherein said inhibiting Trim32 in said cell is expressing a dominant negative Trim 32 protein in said cell.

7. The method of claim 6, wherein said expressing a dominant negative Trim 32 protein in said cell is inserting a synthetic mRNA molecule encoding said dominant negative Trim 32 protein into said cell, said synthetic mRNA molecule comprises a 5-methylcytidine base, a pseudouridine base, or a combination thereof.

8. The method of claim 6, wherein said expressing a dominant negative Trim 32 protein in said cell is delivering a nucleic acid molecule encoding said dominant negative Trim 32 protein via electroporation into said cell.

9. The method of claim 6, wherein said expressing a dominant negative Trim 32 protein in said cell is delivering a nucleic acid molecule encoding said dominant negative Trim 32 protein via a cationic vector into said cell.

10. A method for inducing glucose uptake in a muscle cell in a subject suffering from insulin resistance, comprising the step of increasing the abundance of plakoglobin protein in said cell, thereby inducing glucose uptake in a muscle cell in the subject suffering from insulin resistance.

11. The method of claim 10, wherein said muscle cell is a skeletal muscle cell.

12. The method of claim 10, wherein said increasing the abundance of plakoglobin protein in said cell further results in inducing muscle fiber growth.

13. The method of claim 10, wherein said increasing the abundance of plakoglobin protein in said cell results in inducing the phosphorylation of insulin receptor in said cell.

14. The method of claim 10, wherein said increasing the abundance of plakoglobin protein in said cell is transfecting said cell with a vector comprising a nucleic acid molecule, said nucleic acid molecule encodes said plakoglobin protein.

15. The method of claim 14, wherein said vector comprises a constitutively active promoter.

16. The method of claim 14, wherein said nucleic acid molecule is a synthetic mRNA molecule comprising a 5-methylcytidine base, a pseudouridine base, or a combination thereof.

17. The method of claim 14, wherein said transfecting said cell is via electroporation into said cell.

18. The method of claim 14, wherein said vector is a cationic vector.

* * * * *